United States Patent [19]
Magginetti et al.

[11] Patent Number: 6,087,184
[45] Date of Patent: Jul. 11, 2000

[54] OPPOSABLE-ELEMENT CHROMATOGRAPHIC ASSAY DEVICE FOR DETECTION OF ANALYTES

[75] Inventors: Paul David Magginetti, San Carlos; Daniel Joseph Fitzgerald, Campbell, both of Calif.

[73] Assignee: Beckman Coulter, Inc., Fullerton, Calif.

[21] Appl. No.: 08/967,572

[22] Filed: Nov. 10, 1997

[51] Int. Cl.[7] .................................................. G01N 33/558
[52] U.S. Cl. .............................. 436/514; 422/55; 422/56; 422/58; 422/61; 435/7.1; 435/7.5; 435/7.92; 435/7.94; 435/287.1; 435/287.2; 435/287.7; 435/287.9; 435/805; 435/810; 435/962; 435/970; 436/510; 436/512; 436/513; 436/518; 436/524; 436/525; 436/528; 436/531; 436/169; 436/174; 436/805; 436/810
[58] Field of Search ................................. 422/55–58, 61; 435/7.1, 7.5, 7.92, 7.94, 287.1, 287.2, 287.7, 287.9, 805, 810, 962, 970; 436/510, 512, 513, 514, 518, 524, 525, 528, 531, 533, 534, 65, 164, 169, 174, 175, 177, 178, 800, 805, 810, 814, 817, 818, 825

[56] References Cited

U.S. PATENT DOCUMENTS 5,081,013  1/1992  Rovelli et al. ......................... 435/7.92
5,308,775  5/1994  Donovan et al. ....................... 436/518

*Primary Examiner*—Christopher L. Chin
*Attorney, Agent, or Firm*—William H. May; Margaret A. Kivinski; Gates & Cooper

[57] ABSTRACT

An assay device for detection or determination of an analyte in a sample uses opposable components and is suitable for assay of human chorionic gonadotropin and other protein or glycoprotein hormones. One embodiment of the device comprises: (1) a first opposable component including: (a) a first chromatographic medium having first and second ends and an immobilized first specific binding partner for the analyte in a detection zone; (b) a conjugate pad in operable contact with the first end of the first chromatographic medium, the conjugate pad containing a labeled second specific binding partner for the analyte in resolubilizable form; and (c) a second chromatographic medium having first and second ends and having immobilized thereon in a reference zone a third specific binding partner that specifically binds the labeled second specific binding partner for the analyte and does not bind the analyte, the first end of the second chromatographic medium being in operable contact with the conjugate pad; and (2) a second opposable component including a sample application zone. The assay device can include a timing control to indicate when flow through the chromatographic medium has occurred and the assay can be read, and can also contain a validation zone ensuring that interference from human anti-mouse antibody is not present. Other embodiments of devices are included, as well as methods of use.

50 Claims, 7 Drawing Sheets

OPPOSABLE-ELEMENT CHROMATOGRAPHIC ASSAY DEVICE FOR DETECTION OF ANALYTES

BACKGROUND OF THE INVENTION

This invention is directed to assay devices for determination of characteristics of samples, unitized housings, and methods of determining the characteristics of samples using the assay devices.

Among the many analytical systems used for detection or determination of analytes, particularly analytes of biological interest, are chromatographic assay systems. Among the analytes frequently assayed with such systems are:

(1) hormones, such as human chorionic gonadotropin (hCG), frequently assayed as a marker of human pregnancy, as well as luteinizing hormone (LH), thyroid stimulating hormone (TSH), and follicle stimulating hormone (FSH);

(2) antigens, particularly antigens specific to bacterial, viral, and protozoan pathogens, such as Streptococcus, hepatitis virus, and Giardia;

(3) antibodies, particularly antibodies induced as a result of infection with pathogens, such as antibodies to the bacterium *Helicobacter pylori* and to human immunodeficiency virus (HIV);

(4) other proteins, such as hemoglobin, frequently assayed in determinations of fecal occult blood, an early indicator of gastrointestinal disorders such as colon cancer;

(5) enzymes, such as aspartate aminotransferase, lactate dehydrogenase, alkaline phosphatase, and glutamate dehydrogenase, frequently assayed as indicators of physiological function and tissue damage;

(6) drugs, both therapeutic drugs, such as antibiotics, tranquilizers, and anticonvulsants, and illegal drugs of abuse, such as cocaine, heroin, amphetamines, and marijuana; and (7) vitamins.

Among the most important of such systems are the "thin-layer" systems in which a solvent moves across a thin, flat, absorbent medium. Among the most important of tests that can be performed with such thin-layer systems are immunoassays, which depend on the specific interaction between an antigen or hapten and a corresponding antibody or other specific binding partner. The use of immunoassays as a means for testing for the presence or amount of clinically important molecules has been known for some time. As early as 1956, J. M. Singer reported the use of an immune-based latex agglutination test for detecting a factor associated with rheumatoid arthritis (J. M. Singer et al., *Am. J. Med.*, 22:888–892 (1956)).

Among the chromatographic techniques used in conjunction with immunoassays is a procedure known as immunochromatography. In general, this technique uses a disclosing reagent or particle that has been linked to an antibody to the molecule to be assayed, forming a conjugate. This conjugate is then mixed with a specimen and, if the molecule to be assayed is present in the specimen, the disclosing reagent-linked antibodies bind to the molecule to be assayed, thereby giving an indication that the molecule to be assayed is present. The disclosing reagent or particle can be identifiable by color, magnetic properties, radioactivity, specific reactivity with another molecule, enzymatic activity, or another physical or chemical property. The specific reactions that are employed vary with the nature of the molecule being assayed and the sample to be tested.

Immunochromatographic assays fall into two principal categories: "sandwich" and "competitive," according to the nature of the antigen-antibody complex to be detected and the sequence of reactions required to produce that complex. In general, the sandwich immunochromatographic procedures call for mixing the sample that may contain the analyte to be assayed with antibodies to the analyte. These antibodies are mobile and typically are linked to a label or disclosing reagent, such as dyed latex, a colloidal metal sol, a radioisotope, or an enzyme producing a detectable product. This mixture is then applied to a chromatographic medium containing a band or zone. This band or zone contains immobilized antibodies to the analyte of interest. The chromatographic medium is often in the form of a strip resembling a dipstick. When the complex of the molecule to be assayed and the labeled antibody reaches the zone of the immobilized antibodies on the chromatographic medium, binding occurs and the bound labeled antibodies are localized at the zone. This indicates the presence of the molecule to be assayed. This technique can be used to obtain quantitative or semi-quantitative results.

Examples of sandwich immunoassays performed on test strips are described by U.S. Pat. No. 4,168,146 to Grubb et al. and U.S. Pat. No. 4,366,241 to Tom et al., both of which are incorporated herein by this reference.

In a competitive immunoassay, typically, a labeled analyte or analyte analogue is supplied, and a competitive reaction is set up between the unlabeled analyte in the sample and the labeled analyte or analyte analogue for binding to an immobilized specific binding partner immobilized on the test strip. In general, competitive immunoassays are more suitable for assay of haptens, because they do not require the formation of a ternary sandwich complex.

Although useful, currently available chromatographic techniques using test strips have a number of drawbacks. Many samples, such as fecal samples, contain particulate matter that can clog the pores of the chromatographic medium, greatly hindering the immunochromatographic process. Other samples, such as blood, contain cells and colored components that make it difficult to read the results of the tests. Even if the sample does not create interference, it is frequently difficult with existing chromatographic test devices to apply the sample to the chromatographic medium so that the sample front moves uniformly through the chromatographic medium to ensure that the sample reaches the area where the binding is to occur in a uniform, straight-line manner.

Sample preparation and waste generation are responsible for other problems with currently available devices and techniques for immunochromatography. The increased prevalence of diseases spread by infected blood and blood fractions, such as AIDS and hepatitis, has exacerbated these problems. It is rarely possible to apply a sample (such as feces) or a sampling device (such as a throat swab) directly to the chromatographic medium. Several extraction and pretreatment reactions are usually required before the sample can be applied to the chromatographic medium. These reactions are typically carried out by the physician or technician performing the test in several small vessels, such as test tubes or microfuge tubes, requiring the use of transfer devices such as pipettes. Each of these devices is then contaminated and must be disposed of using special precautions so that workers or people who might inadvertently come into contact with the waste do not become contaminated and subject to infection by infectious agents contained in the waste.

Additionally, such a device should be capable of receiving a possibly contaminated sample or a sample preparation device directly so as to eliminate the need for extraction vessels and transfer devices. Such a device, preferably in the form of a test strip, should also be capable of performing immunochromatographic assays on colored samples or samples containing particulates without interference and should be able to deliver the sample to the chromatographic medium uniformly and evenly to improve accuracy and precision of the test. This aspect of an improved assay device is particularly important in avoiding false negatives and false positives.

Another aspect in which present immunochromatographic test devices need improvement is in reducing the volume of sample required to achieve the threshold sensitivity of the analyte to be determined. This is particularly important if the sample is whole blood and the donor is an infant, pediatric patient, geriatric patient, or patient who has suffered blood loss, limiting the volume of blood that can be drawn. If multiple tests are to be performed, as is often the case, it is crucial that the minimum volume of blood be used for each test. In addition, improvement is needed in allowing the more rapid performance of assays on immunochromatographic test strips to allow for the formation of a stable reaction endpoint in the shortest possible interval of time and to allow for a period where the color intensity of the reaction zones is stable for an additional period of time, allowing the operator to record an accurate result for a period of time, i.e., providing a stable reading window. This improves operator convenience and reduces the likelihood of error.

Another improvement in immunochromatographic assay test devices and formats is related to the use of monoclonal antibodies in assay test formats, particularly for assay of hCG. Although monoclonal antibodies can yield an increase in sensitivity and specificity for such assays, they can cause additional problems, particularly when murine monoclonal antibodies are used. If a plasma or serum sample is used, the human-anti-murine antibody (HAMA) response can cause interference in the assay, such as the occurrence of false negative or false positive results, when monoclonal antibodies are used.

Additionally, there is a need for assay devices that provide an accurate indication to the user that the assay has been completed. If the assay device is read before the assay has gone to completion, then an inaccurate result is very likely obtained. If the user cannot be certain when the reaction has been completed, the user is liable to wait an extended period of time, which is inefficient. Therefore, it would be desirable to have an assay device that would precisely indicate to the user when chromatography has occurred through the medium, so that the assay can be read and interpreted.

Additionally, it would be desirable to have an assay device that gives a semiquantitative indication of the concentration of the analyte assayed in a single test device so that a comparison can be made with a concentration standard. If a single test device cannot be used for such a comparison, a series of controls must be run in a number of separate test devices. It would therefore be desirable to have an assay device that can provide such a semi-quantitative indication in a single device with the use of a single sample.

Accordingly, there is a need for an assay device that gives a precise indication of the performance of the assay and for a device that can use monoclonal antibodies and control for the existence of HAMA. There is further a need for an immunochromatographic device that can efficiently assay a large number of analytes and utilize internal controls to indicate efficient performance of the assay. There is also a need for an improved immunochromatographic assay device that can give a semiquantitative indication of analyte concentration by comparison with a standard.

SUMMARY

We have developed assay devices that meet these needs and provide improved assays for analytes of biological interest, particularly protein and glycoprotein hormones, such as hCG, TSH, LH, or FSH, while simplifying the performance of the assay and avoiding contamination. The devices can perform all types of immunoassays, including sandwich immunoassays, competitive immunoassays, and assays employing combinations of these principles, but are particularly adapted to the performance of sandwich immunoassays.

One embodiment of an assay device according to the present invention comprises:

(1) a first opposable component including:
    (a) a first chromatographic medium having first and second ends and an immobilized first specific binding partner for the analyte in a detection zone;
    (b) a conjugate pad in operable contact with the first end of the first chromatographic medium, the conjugate pad including:
        (i) a first portion containing a labeled second specific binding partner for the analyte in resolubilizable form;
        (ii) a second portion; and
        (iii) a third portion containing a labeled second specific binding partner for the analyte in resolubilizable form, the second portion separating the first portion and the third portion; and
    (c) a second chromatographic medium having first and second ends and having immobilized thereon in a reference zone a third specific binding partner, other than the analyte or an analyte analogue, that specifically binds the labeled second specific binding partner for the analyte and does not bind the analyte, the first end of the second chromatographic medium being in operable contact with the conjugate pad; and (2) a second opposable component including a sample application zone.

In this embodiment of an assay device according to the present invention, the first and second opposable components are brought into opposition to apply a sample applied to the sample application zone to the conjugate pad to resolubilize the labeled second specific binding partner and so that the sample and the resolubilized labeled second specific binding partner in the first portion of the conjugate pad are applied to the first chromatographic medium and the sample and the resolubilized labeled second specific binding partner in the third portion of the conjugate pad are applied to the second chromatographic medium for detection of the analyte.

Typically, the label is a colloidal particle label. Preferably, the colloidal particle label is a colloidal carbon label, although other colloidal labels can be used. Preferably, the label is a visually detectable label; this category of labels includes colloidal particle labels.

In one preferred alternative, the quantity of third specific binding partner in the reference zone is predetermined so that the quantity of labeled second specific binding partner binding to the third specific binding partner gives an intensity of label at the reference zone equivalent to that given in the detection zone when a predetermined concentration of analyte is present in the sample. This allows for at least a semiquantitative determination of analyte concentration and for a determination of whether or not the analyte concentration is above or below a clinically important level.

The sample application zone can contain at least one reagent for treatment of the sample.

The analyte can be selected from the group consisting of chorionic gonadotropin (hCG), luteinizing hormone (LH), follicle stimulating hormone (FSH), thyroid stimulating hormone (TSH), corticotropin-releasing hormone (CRH), growth hormone-releasing hormone (GHRH), prolactin, human growth hormone (hGH), β-lipotropin, corticotropin, β-endorphin, calcitonin, parathormone, human placental lactogen (hPL), insulin, glucagon, pancreatic polypeptide (PP), secretin, cholecystokinin-pancreozymin, motilin, vasoactive intestinal peptide, gastric inhibitory peptide, and erythropoietin. Typically, the analyte is hCG, LH, FSH, or TSH. In one particularly preferred alternative, the analyte is human chorionic gonadotropin (hCG). When hCG is the analyte, preferably the first specific binding partner is a monoclonal antibody specific for the ax subunit of hCG and the second specific binding partner is a monoclonal antibody specific for the β subunit of hCG and not cross-reactive with luteinizing hormone. Other pairings of monoclonal antibodies can alternatively be used; for example, the first specific binding partner can be a monoclonal antibody specific for the , subunit of hCG and not cross-reactive with luteinizing hormone, and the second specific binding partner can be a monoclonal antibody specific for the a subunit of hCG.

In a preferred alternative, the first opposable component further includes a resolubilizable visible dye, which can be located either in an area between the detection zone and the second end of the first chromatographic medium or in an absorber that is optionally present and the second opposable component has an aperture for viewing of the visible dye when flow has occurred through the first chromatographic medium and the assay can be read and interpreted.

In a variation of this preferred alternative, the first chromatographic medium further includes: (i) a resolubilizable visible dye linked to a first member of an auxiliary specific binding pair that does not bind to any other specific binding partner in the device or to the analyte in an area between the detection zone and the second end of the first chromatographic medium and (ii) an immobilized second member of the auxiliary specific binding pair that binds only the first member of the auxiliary specific binding pair in a dye viewing area, and the second opposable component has an aperture for viewing of the visible dye when flow has occurred through the first chromatographic medium and the assay can be read and interpreted. Typically, in this variation, the first member of the auxiliary specific binding pair is biotin and the second member of the auxiliary specific binding pair is avidin or streptavidin. The resolubilizable visible dye can be located either in an area between the detection zone and the second end of the first chromatographic medium or in an absorber that is optionally present, as described above.

In another preferred alternative, the sample application zone contains a fourth specific binding partner that is specific for human antibodies that bind the second specific binding partner. In this preferred alternative, the first chromatographic medium contains in a validation zone, a fifth immobilized specific binding partner that is specific for human antibodies that bind the second specific binding partner such that the presence of detectable label at the validation zone indicates interference, the validation zone being located closer to the first end of the first chromatographic medium than is the detection zone. Typically, in this alternative, the second specific binding partner is a non-human monoclonal antibody, the fourth specific binding partner is specific for human IgG antibodies that bind to the non-human monoclonal antibody, and the fifth immobilized specific binding partner is specific for human IgG antibodies that bind to the non-human monoclonal antibody. The fourth specific binding partner can be immobilized in the sample application zone. Alternatively, the fourth specific binding partner can be mobile and located at the sample application zone. Typically, in this alternative, the first and second specific binding partners are murine monoclonal antibodies, and the fourth and fifth specific binding partners are each murine IgG or a derivative or polymer of murine IgG.

Another embodiment of an assay device according to the present invention comprises:
(1) a first opposable component including:
  (a) a chromatographic medium having two separated functional zones:
    (i) a first functional zone having thereon an immobilized first specific binding partner for the analyte in a detection zone;
    (ii) a second functional zone having thereon in a reference zone an immobilized third specific binding partner, other than the analyte or an analyte analogue, that specifically binds a labeled second specific binding partner for the analyte and does not bind the analyte; and
  (b) a conjugate pad in operable contact with the chromatographic medium between the first and second functional zones, the conjugate pad dividing the first functional zone from the second functional zone, the conjugate pad including:
    (i) a first portion containing a labeled second specific binding partner for the analyte in resolubilizable form;
    (ii) a second portion; and
    (iii) a third portion containing a labeled second specific binding partner for the analyte in resolubilizable form, the second portion separating the first portion and the third portion; and
(2) a second opposable component having a sample application zone.

In this embodiment, the first and second opposable components are brought into operable contact to apply a sample applied to the sample application zone to the conjugate pad to resolubilize the labeled second specific binding partner for the analyte in the first and third portions of the sample application zone and so that the sample and the resolubilized labeled second specific binding partner in the first portion of the sample application zone flow through the first functional zone of the chromatographic medium and the sample and the resolubilized labeled second specific binding partner in the third portion of the sample application zone flow through the second functional zone of the chromatographic medium.

This embodiment is substantially similar to the first embodiment except that one chromatographic medium is used, divided into two functional zones.

In a preferred version of this embodiment, the chromatographic medium further includes a resolubilizable visible dye in an area between the detection zone and the first end of the chromatographic medium, and the second opposable component has an aperture for viewing of the visible dye when flow has occurred through the chromatographic medium and the assay can be read and interpreted. Alternatively, as described above, the chromatographic medium further includes: (i) a resolubilizable visible dye linked to a first member of an auxiliary specific binding pair that does not bind to any other specific binding partner in the device or to the analyte in an area between the detection zone and the first end of the chromatographic medium and (ii) an immobilized second member of the auxiliary specific binding pair that binds only the first member of the auxiliary specific binding pair in a dye viewing area, and the second opposable component has an aperture for viewing of the visible dye when flow has occurred through the chromatographic medium and the assay can be read and interpreted.

This embodiment can also employ fourth and fifth specific binding partners as described above. In this alternative, the fifth specific binding partner is located in a validation zone that is between the conjugate pad and the detection zone.

Yet another embodiment of an assay device according to the present invention comprises:

(1) a first opposable component including:
 (a) a first chromatographic medium having first and second ends and an immobilized first specific binding partner for the analyte in a detection zone;
 (b) a conjugate pad including:
  (i) a first portion containing a labeled second specific binding partner for the analyte in resolubilizable form;
  (ii) a second portion; and
  (iii) a third portion containing a labeled fourth specific binding partner for the analyte in resolubilizable form that binds a third specific binding partner, the second portion separating the first portion and the third portion; and
 (c) a second chromatographic medium having first and second ends and having immobilized thereon in a reference zone a third specific binding partner, other than the analyte or an analyte analogue, that specifically binds the labeled fourth specific binding partner and does not bind the analyte or the labeled second specific binding partner for the analyte, the first end of the first chromatographic medium and the first end of the second chromatographic medium being in operable contact with the conjugate pad; and
(2) a second opposable component including a sample application zone.

In this embodiment, the first and second opposable components are brought into opposition to apply a sample applied to the sample application zone to the conjugate pad to resolubilize the labeled second specific binding partner and the labeled fourth specific binding partner and so that the sample and the resolubilized labeled second specific binding partner are applied to the first chromatographic medium and the sample and the resolubilized labeled fourth specific binding partner are applied to the second chromatographic medium for detection of the analyte.

This embodiment uses two labeled specific binding partners, one binding to the analyte bound to the detection zone and the other binding to the reference zone. Typically, the labels of the labeled specific binding partners are identical.

Another embodiment of an assay device according to the present invention comprises:

(1) a first opposable component including:
 (a) a chromatographic medium having two separated functional zones:
  (i) a first functional zone having thereon an immobilized first specific binding partner for the analyte in a detection zone;
  (ii) a second functional zone having thereon in a reference zone an immobilized third specific binding partner, other than the analyte or an analyte analogue, that specifically binds a labeled fourth specific binding partner and does not bind the analyte or a specific binding partner that specifically binds the analyte; and
 (b) a conjugate pad in operable contact with the chromatographic medium between the first and second functional zones, the conjugate pad dividing the first functional zone from the second functional zone, the conjugate pad including:
  (i) a first portion containing a labeled second specific binding partner for the analyte in resolubilizable form;
  (ii) a second portion; and
  (iii) a third portion containing a labeled fourth specific binding partner for the analyte in resolubilizable form that binds the third specific binding partner, the second portion separating the first portion and the third portion; and
(2) a second opposable component having a sample application zone.

In this embodiment, the first and second opposable components are brought into operable contact to apply a sample applied to the sample application zone to the conjugate pad to resolubilize the labeled second specific binding partner for the analyte and so that the sample and the resolubilized labeled second specific binding partner flow through the first functional zone of the chromatographic medium and the sample and the resolubilized labeled fourth specific binding partner flow through the second functional zone of the chromatographic medium.

This embodiment is substantially similar to the one described immediately above except that it uses a single chromatographic medium divided into two functional zones by a conjugate pad.

Yet another embodiment of an assay device according to the present invention replaces the third specific binding partner in the conjugate zone with an analyte or analyte analogue to provide an onboard control. This embodiment can use either two chromatographic media or one chromatographic medium divided into two functional zones.

When two chromatographic media are used, the device comprises:

(1) a first opposable component including:
 (a) a first chromatographic medium having first and second ends and an immobilized first specific binding partner for the analyte in a detection zone;
 (b) a conjugate pad in operable contact with the first end of the first chromatographic medium, the conjugate pad including:
  (i) a first portion containing a labeled second specific binding partner for the analyte in resolubilizable form;
  (ii) a second portion; and
  (iii) a third portion containing a labeled second specific binding partner for the analyte in resolubilizable form, the second portion separating the first portion from the third portion; and
 (c) a second chromatographic medium having first and second ends and having immobilized thereon in a control zone the analyte or an analyte analogue, the first end of the first chromatographic medium and the first end of the second chromatographic medium being in operable contact with the conjugate pad; and
(2) a second opposable component including a sample application zone.

In this embodiment, the first and second opposable components are brought into opposition to apply a sample applied to the sample application zone to the conjugate pad to resolubilize the labeled second specific binding partner and so that the sample and the resolubilized labeled second specific binding partner in the first portion of the conjugate pad are applied to the first chromatographic medium and the sample and the resolubilized labeled second specific binding partner in the third portion of the conjugate pad are applied to the second chromatographic medium for detection of the analyte.

When one chromatographic medium is used divided into two functional zones, the device comprises:

(1) a first opposable component including:
   (a) a chromatographic medium having two separated functional zones:
      (i) a first functional zone having thereon an immobilized first specific binding partner for the analyte in a detection zone;
      (ii) a second functional zone having thereon in a control zone an immobilized analyte or analyte analogue; and
   (b) a conjugate pad in operable contact with the chromatographic medium between the first and second functional zones, the conjugate pad dividing the first functional zone from the second functional zone, the conjugate pad including:
      (i) a first portion containing a labeled second specific binding partner for the analyte in resolubilizable form;
      (ii) a second portion; and
      (iii) a third portion containing a labeled second specific binding partner for the analyte in resolubilizable form, the second portion separating the first portion from the third portion; and (2) a second opposable component having a sample application zone.

In this embodiment, the first and second opposable components are brought into operable contact to apply a sample applied to the sample application zone to the conjugate pad to resolubilize the labeled second specific binding partner for the analyte and so that the sample and the resolubilized labeled second specific binding partner from the first portion flow through the first functional zone of the chromatographic medium and the sample and the resolubilized labeled second specific binding partner from the third portion flow through the second functional zone of the chromatographic medium.

In either of these last two embodiments, the quantity of analyte or analyte analogue in the control zone can be predetermined so that the quantity of labeled second specific binding partner binding to the analyte or analyte analogue gives an intensity of label at the control zone equivalent to that given in the detection zone when a predetermined concentration of analyte is present in the sample.

Another aspect of the present invention is methods of detecting or determining analytes using assay devices according to the present invention.

BRIEF DESCRIPTION OF THE DRAWINGS

These and other features, aspects, and advantages of the present invention will become better understood with reference to the following description, appended claims, and accompanying drawings where:

DESCRIPTION

Definitions

Figure 1:
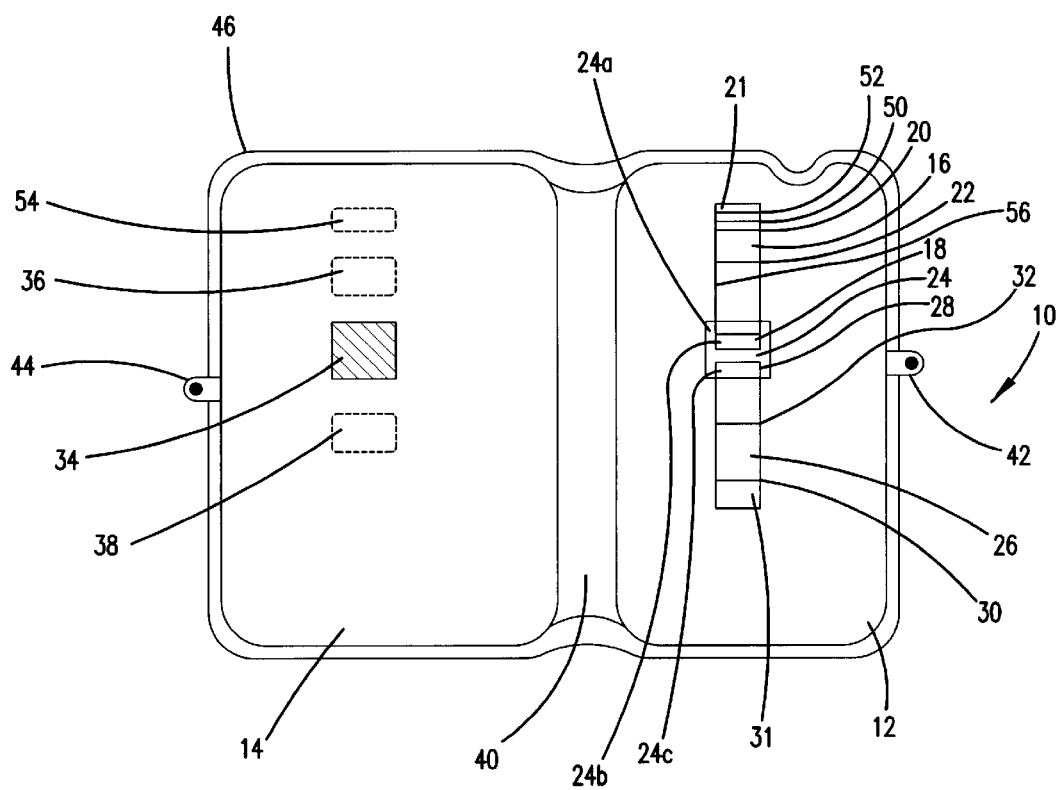
FIG. 1 is a drawing of a first embodiment of an assay device according to the present invention with two chromatographic media and employing two labeled specific binding partners.

In the context of this disclosure, the following terms are defined as follows unless otherwise indicated:

Specific binding partner: A member of a pair of molecules that interact by means of specific noncovalent interactions that depend on the three-dimensional structures of the molecules involved. Typical pairs of specific binding partners include antigen-antibody, hapten-antibody, hormone-receptor, nucleic acid strand-complementary nucleic acid strand, substrate-enzyme, inhibitor-enzyme, carbohydrate-lectin, biotin-avidin, and virus-cellular receptor.

Operable contact: Two solid components are in operable contact when they are in contact, either directly or indirectly, in such a manner that a liquid can flow from one of the two components to the other substantially uninterruptedly, by capillarity or otherwise. "Direct contact" means the two elements are in physical contact, such as edge-to-edge or front-to-back. "Indirect contact" means the two elements are not in physical contact, but are bridged by one or more conducting means. This bridging by one or more conducting means could be either edge-to-edge or front-to-back, such as by the opposition or bringing into contact of planar elements.

Analyte: The term "analyte" includes both the actual molecule to be assayed and analogues and derivatives thereof when such analogues and derivatives bind another molecule used in the assay in a manner substantially equivalent to that of the analyte itself.

Antibody: The term "antibody" includes both intact antibody molecules of the appropriate specificity and antibody fragments (including Fab, F(ab'), F(ab')$_2$, and Fv fragments), as well as chemically modified intact molecules and antibody fragments, including hybrid molecules assembled by in vitro reassociation of subunits. Also included are genetically engineered antibodies of the appropriate specificity, including single-chain derivatives. Both polyclonal and monoclonal antibodies are included unless otherwise specified.

Label: The term "label" is used herein to refer to any directly or indirectly detectable or determinable moiety that is covalently or noncovalently associated with a specific binding partner that binds one or more specific binding partners that participate in an assay performed by a device according to the present invention. Typically, the term "label" is used to refer only to the detectable moiety itself; the term "labeled specific binding partner" is used to refer to the covalent conjugate or noncovalent complex of the label and the specific binding partner. Labels useful in devices according to the present invention are described below.

Secondary specific binding partner: The term "secondary specific binding partner" is used to designate an additional specific binding partner that binds to a member of a pair of specific binding partners when the pair of specific binding partners is interacting. For example, a pair of specific binding partners can comprise Giardia antigen and rabbit anti-Giardia antibody. In that case, the secondary specific binding partner can be goat anti-rabbit IgG antibody. The secondary specific binding partner can be specific for the species, class, or subclass of an antibody specific binding partner to which it binds. Alternatively, when one of the specific binding partners is labeled with biotin, the secondary specific binding partner can comprise a molecule conjugated to avidin or streptavidin.

Sample: The term "sample" as used herein, refers to any fluid that can be applied to the assay device, directly or indirectly, and that contains or may contain an analyte, including, but not limited to, serum, plasma, whole blood, saliva, urine, cerebrospinal fluid, fecal extracts, material contained in a swab, such as a throat swab, or other fluids.

Interference: The term "interference" as used herein in conjunction with reference to the human anti-murine antibody (HAMA) response, refers to either the existence of false negative or false positive results that would be caused by the presence of HAMA in a sample of human origin.

I. Chromatographic Assay Devices

One aspect of the present invention comprises chromatographic assay devices particularly useful for the assay of analytes in biological samples. These devices are suitable for the direct application of biological samples, without preliminary extraction steps, and are constructed so as to minimize interference with assay results caused by particulates or colored samples. These devices are intended to provided more homogeneous mixing of the analyte and a labeled specific binding partner that is typically in resolubilizable form.

The device has at least two opposable components, typically substantially planar. One of these substantially planar components has on its surface a chromatographic medium. When there are two opposable components, one of the opposable components is designated the first opposable component and the other is designated the second opposable component. Typically, the first opposable component is the component with the chromatographic medium. This distinction is arbitrary and for convenience in description; the role of each of the opposable components is determined by the element or elements located on it.

The device also has means for opposing the opposable components, also referred to as bringing them into operable contact, and applying pressure thereto. The opposable components can be brought into opposition from a position in which they are not in opposition by direct manual closure, i.e., by manipulation by the operator. The pressure applied is sufficient to transfer fluid from one opposable component to another opposable component in a direction substantially normal to the opposable components in a sequence determined by the construction of the assay device. The end result is that the sample is applied to the chromatographic medium for detection or determination of the analyte thereon. The pressure also drives the fluid through the chromatographic medium to accelerate the process of chromatography, giving a detectable result in less time. Additionally, the pressure makes possible the performance of steps, such as extraction steps, in the device, and can be used to remove excess fluid from the chromatographic medium by absorbers to reduce the background of the assays. The pressure is generated by placing the opposable components into opposition and maintained by holding the components in opposition by engagers such as locks or clasps or, alternatively, by an adhesive strip along the outside margin of one of the components that allows sealing the components.

Devices according to the present invention can be constructed for the performance of either a sandwich or a competitive assay; the devices according to the present invention are particularly useful for sandwich immunoassays. As used herein, the term "immunoassay" is used generally to include specific binding assays and need not necessarily be restricted to assays in which any or all of the specific binding partners are antibodies, unless so specified.

The degree of pressure employed in the device can be regulated so that it is optimum for the characteristics of the chromatographic medium, analyte, and label.

Assay methods using a device according to the present invention can give a qualitative, semi-quantitative, or quantitative indication of analyte presence or concentration, depending upon the concentration of the labeled specific binding partner at the detection zone and the size of the detection zone, as well as the detection method used. In general, in the specification, the term "detect" is used to refer to a qualitative indication of the presence or absence of an analyte, while the term "determine" is used to refer to either a semi-quantitative or a quantitative determination of the concentration of the analyte. The term "observe" is typically used to refer to a visual observation leading to a qualitative or semi-quantitative determination or detection of analyte presence or concentration, while the term "measure" is typically used to refer to an instrumental measurement that yields a quantitative determination of analyte concentration. Such a measurement is typically by spectroscopy, although other methods can be used.

A. Elements Common to Devices According to the Present Invention

A number of elements are common to assay devices according to the present invention and are discussed here for convenience.

1. The Chromatographic Medium

The chromatographic medium is a strip. Typically, the strip is substantially planar, although this is not required in all applications. It is typically rectangular, having first and second ends and first and second surfaces and can be divided into two or more functional zones. Throughout this description, the term "first end" refers to the end at or near which liquid is applied to the chromatographic medium and the term "second end" applies to the opposite end of the chromatographic medium. Liquid applied at or near the first end of the chromatographic medium can be, but is not necessarily, a sample or a treated sample, and can contain a resolubilized labeled specific binding partner for the analyte.

Alternatively, as indicated below, the chromatographic medium can contain a zone of resolubilizable labeled specific binding partner for the analyte in a zone referred to as a "conjugate zone."

The chromatographic medium is composed of material suitable as a medium for thin-layer chromatography of analyte and analyte-antibody conjugates, such as nitrocellulose, nylon, rayon, cellulose, paper, or silica. Preferably, the chromatographic medium is nitrocellulose. The chromatographic medium can be pretreated or modified as needed. Typically, the chromatographic medium is translucent, so that the colored zones appearing on it can be viewed from either side, such as through an aperture.

2. Absorbers

In a number of devices according to the present invention, absorbers can be brought into operable contact with at least one end of the chromatographic medium. The absorbers can be made of any bibulous material that will hold a liquid sufficiently so that liquid can be drawn through the chromatographic medium and accumulated in the absorber. Typical materials for the absorber include, but are not limited to, cellulose and filter paper. A preferred material for the absorbers of the embodiments described herein is cellulose. The size and shape of the absorber can be chosen according to the volume of fluid used in the assay.

In some alternatives, one or more than one of the absorbers can have incorporated therein a resolubilizable reagent, such as a dye, intended to migrate when fluid reaches the absorber. This alternative is described further below.

3. Other Fluid-Carrying Elements

As described below, in particular devices according to the present invention, other fluid-carrying elements can be employed as sample application zones, conjugate pads, applicators, or conductors. These elements are typically prepared of hydrophilic media that pass liquids without substantially absorbing them. Such materials are well known in the art. One preferred material for the conjugate pad in assay devices according to the present invention is non-woven polyester. One preferred material for the sample application zone in assay devices according to the present invention is extruded cellulose acetate. In some cases, these elements can have incorporated therein a component in dry form that can be resolubilized by addition of a liquid to the element, typically an aqueous liquid. The terms "resolubilized," "resolubilizable," and similar terminology are used herein generally to refer to the state of such components.

4. Opposable Components

Many of the embodiments of the assay device according to the present invention comprise two opposable components. The bodies of the opposable components are preferably made of laminated cardboard that is sufficiently impervious to moisture to contain liquids involved in the performance of the assay carried out by the device. Other cellulose-based materials, such as paperboard or solid bleached sulfite (SBS) can also be used. Alternatively, the bodies of the opposable components can be made of plastic that is impervious to moisture. A suitable plastic is polycarbonate plastic such as Lexan®.

The opposable components are joined by a hinge, preferably made of a material impermeable to liquids, such as coated solid bleached sulfite or a plastic that can be compatibly joined with or is the same as the material used for the first and second opposable components.

5. Labeled Components

For assay devices intended to perform a sandwich immunoassay, the labeled component is typically a labeled specific binding partner to the analyte. This labeled component is typically mobile, in that it can migrate through the chromatographic medium, whether free or bound to analyte. The label is preferably a visually detectable label, such as a colloidal label. The colloidal label can either be a colloidal metal label or a non-metallic colloidal label. A preferred non-metallic colloidal label is colloidal carbon. Colloidal carbon labels for labeling of specific binding partners are described, for example, in U.S. Pat. No. 5,529,901 to Van Doom et al., incorporated by this reference. In general, a suitable colloidal carbon label is prepared from carbon black powder charcoal of the appropriate grade. Suitable carbon black powder charcoal is an amorphous black solid in the form of a fine powder with no odor, has a melting point of 3000° C., has a specific gravity of 1.7 to 1.9, has a pH greater than 7 when measured with 50 grams in 1 liter of water, and has a particle size of 25 nm. Additionally, it is strongly preferred that such carbon powder produce a carbon sol in an aqueous medium, such as pure water or a buffer system of low ionic strength, that does not require an added stabilizing agent to be stable. The stability of carbon sols in the absence of added stabilizing agent can be predicted on the basis of three properties of the carbon particles: the dibutylphthalate adsorption, the volatile content, and the average primary particle diameter.

From these particles, carbon sols can be prepared by a variety of techniques, including ultrasonification, shaking or boiling (with or without stirring) a mixture of carbon particles and an aqueous medium without stabilizing agents.

Specific binding partners such as antibodies can be bound to carbon sols by noncovalent interactions. Although Applicants do not intend to be bound by this theory, it is likely that the noncovalent interactions involve hydrophobic interactions between the specific binding partner and the carbon sol.

Sonification of carbon powder in pure water or in a buffer of low ionic strength, followed by mixing the colloidal carbon suspension with a suspension of a macromolecule such as a specific binding partner, i.e., an antibody, in the same buffer under gentle mixing, results in conjugates of the specific binding partner with the carbon sol label suitable for use with immunoassay devices according to the present invention.

Alternatively, addition of a suspension of a macromolecular specific binding partner in a buffer of low ionic strength, with the final macromolecular concentration at the minimal protective amount, to a mixture of carbon powder and water during a short homogenization step by sonification leads to the formation of conjugates of the specific binding partner with the carbon sol label.

If a colloidal metal label is used, preferably, the colloidal metal label is gold, silver, bronze, iron, or tin; most preferably, it is gold. The preparation of gold labeled antibodies and antigens is described in J. DeMey, "The Preparation and Use of Gold Probes" in *Immunocytochemistry: Modern Methods and Applications* (J. M. Polak & S. VanNoorden, eds., Wright, Bristol, England, 1986), ch. 8, pp. 115–145, incorporated herein by this reference. Antibodies labeled with colloidal gold are commercially available, such as from Sigma Chemical Company, St. Louis, Mo.

Alternatively, still other colloidal labels, such as a dye-silica label, can also be used.

As another alternative, liposomal labels carrying a visible dye or other visible marker can be used. These labels are well known in the art and need not be described further here.

In a less preferred alternative, the visually detectable label can be a colored latex label such as a polystyrene latex label. It is also possible to use other labels, such as a radioactive label, a fluorescent label, or an enzyme label. These labels are also well known in the art and need not be described further here.

Typically, the resolubilizable labeled specific binding partner is located in a conjugate pad, although other arrangements are possible for incorporation of the resolubilizable labeled specific binding partner in the test device. If a conjugate pad is used, the conjugate pad is a fluid-carrying element of the type described above.

In some cases, there is more than one labeled component. For example, some assay devices according to the present invention make use of two separate labeled components. When there is more than one labeled component, the labels of the labeled components can be identical or can be different. Typically, the labels are identical; however, it is also possible to use two labels that give different visual indications, such as different colors.

B. Details of Devices According to the Present Invention

1. Device Having Two Chromatographic Media and Conjugate Pad with Two Labeled Specific Binding Partners One embodiment of assay devices according to the present invention has two chromatographic media and a conjugate pad that bridges the two chromatographic media. This device is shown in FIG. 1.

For convenience in referring to them below, the specific binding partners used in this embodiment, including optional specific binding partners, are recited below:

The first specific binding partner is an immobilized, unlabeled, specific binding partner that binds the analyte, located in a detection zone. The second specific binding partner is a mobile labeled specific binding partner for the analyte located in a conjugate pad. The third specific binding partner is an immobilized, unlabeled specific binding partner, other than the analyte or an analyte analogue, that is located in a reference zone and that does not bind the analyte or a specific binding partner that binds the analyte. The third specific binding partner binds a labeled fourth specific binding partner described below. The fourth specific binding partner is a mobile labeled specific binding partner that is located in the conjugate pad, in a separate region from the second specific binding partner, and binds the third specific binding partner. The fourth specific binding partner does not bind the analyte or any specific binding partner that binds the analyte. The fifth specific binding partner, whose use is optional but preferable, is located in a sample application zone and is unlabeled; it is specific for human antibodies that bind the second specific binding partner. Typically, when the fifth specific binding partner is used, the second specific binding partner is a non-human monoclonal antibody as described further below and the fifth specific binding partner is specific for human antibodies that bind the non-human monoclonal antibody. The fifth specific binding partner can be either immobilized or mobile. The sixth specific binding partner, whose use is also optional but preferable, is used along with the fifth specific binding partner; it is unlabeled, immobilized in a validation zone, and is also specific for human antibodies that bind the second specific binding partner. Again, typically, when the fifth and sixth specific binding partners are used, the second specific binding partner is a non-human monoclonal antibody, as indicated.

The device 10 has first and second opposable components 12 and 14. The first opposable component 12 includes a first chromatographic medium 16 with a first end 18 and a second end 20. Optionally, the second end 20 of the first chromatographic medium 16 can be in operable contact with a first absorber 21. The first chromatographic medium 16 has immobilized thereon in a detection zone 22 the first specific binding partner as described above, i.e., an unlabeled specific binding partner that binds the analyte. The first opposable component 12 further includes a conjugate pad 24. The conjugate pad 24 is in operable contact with the first end 18 of the first chromatographic medium 16. The first opposable component 12 further includes a second chromatographic medium 26 having first and second ends 28 and 30. Optionally, the second end 30 of the second chromatographic medium 26 is in operable contact with a second absorber 31. The second chromatographic medium 26 has immobilized thereon in a reference zone 32 the third specific binding partner as described above. This specific binding partner specifically binds the labeled fourth specific binding partner, as described above, but does not bind the analyte or a labeled specific binding partner to the analyte; it is other than the analyte or an analyte analogue. The third specific binding partner in the reference zone 32 is unlabeled. The first end 28 of the second chromatographic medium 26 is in operable contact with the conjugate pad 24.

The conjugate pad 24 preferably is divided into three portions. The first portion 24a contains a labeled specific binding partner that is specific for the analyte in resolubilizable form. This specific binding partner is the second specific binding partner defined above. The second portion 24b contains an inert stabilizing medium such as conjugate diluent. The third portion 24c contains a labeled fourth specific binding partner, in resolubilizable form, that specifically binds the third specific binding partner. The fourth specific binding partner does not bind the analyte or any specific binding partner that binds the analyte. The first portion 24a and the third portion 24c are functionally isolated so that when a liquid is added to the conjugate pad 24, the second specific binding partner in the first portion 24a migrates substantially only into the first chromatographic medium 16, and the fourth specific binding partner in the third portion 24c migrates substantially only into the second chromatographic medium 26.

The second opposable component 14 includes a sample application zone 34. The second opposable component also includes a first aperture 36 for viewing of the detection zone 22 and a second aperture 38 for viewing of the reference zone 32. The first and second opposable components 12 and 14 are joined by a hinge 40.

The first and second opposable components 12 and 14 preferably further comprise engagers that secure the first and second opposable components 12 and 14 in opposition or operable contact. The engagers can comprise locks, such as locks 42 and 44, that are engaged when the first opposable component 12 and the second opposable component 14 are brought into opposition. The construction and dimensions of the locks 42 and 44 can be varied to exert the optimal degree of pressure on the opposable components 12 and 14. The degree of pressure that is optimal can depend on the thickness of construction of the first chromatographic medium 16, the second chromatographic medium 26, the intended sample volume, and other factors. Alternatively, the first and second opposable components 12 and 14 can be held in position by means of an adhesive strip that is applied to one of the first or second opposable components 12 and 14; the adhesive strip can be provided with a release liner. To guard against leakage of samples or reagents, a sealing ridge or gasket 46 can be positioned around the perimeter of the first and second opposable components 12 and 14. Although the use of the engagers, such as locks 42 and 44 or, alternatively, the adhesive strip, and the use of the sealing ridge or gasket 46, is generally preferred, these elements are not necessary to construct a basic device according to the present invention.

Alternatively, the opposable components can be incorporated into a housing with a bevel closure, such as that disclosed in U.S. Pat. No. 5,441,698 to Norell, incorporated herein. The bevel closure acts as a locking device in this alternative and is therefore an alternative to separate engagers such as locks.

In one particularly preferred alternative of the device according to the present invention, the first opposable component 12 further includes a dye area 50 and a dye viewing area 52. The dye area 50 and the dye viewing area 52 can be located in the first absorber 21 as shown in FIG. 1. Alternatively, the dye area 50 and the dye viewing area 52 can be located between the detection zone 22 and the second end 20 of the first chromatographic medium 16. The dye area 50 has a resolubilizable visible dye. During the performance of the assay, the dye in the dye area 50 is resolubilized and migrates from the dye area 50 to the dye viewing area 52. In this alternative, the second opposable component 14 further includes a dye aperture 54 allowing viewing of the dye viewing area 52 on the first opposable component 12. The dye aperture 54 on the second opposable component 14 is located so that the dye area 50 on the first opposable component 12 is not visible before migration of the dye has occurred from the dye area 50 to the dye viewing area 52. This gives a visual indication that flow through the first chromatographic medium has occurred, that the flow is functional, and that the assay can be read and interpreted. The first absorber 21 can make operable contact with the first chromatographic medium 16 by overlapping the first chromatographic medium 16 at its second end 20 so that the dye area 50 and the dye viewing area 52 are located in the region of overlap, either on the first absorber 21 or the first chromatographic medium 16. A similar overlap arrangement can be used for other embodiments of the present invention that use a dye area and a dye viewing area.

In an alternative, the dye area 50 contains a resolubilizable visible dye linked to a first member of an auxiliary specific binding pair that does not bind to any other specific binding partner in the device or to the analyte, and the dye viewing area 52 contains an immobilized second member of the auxiliary specific binding pair that binds only the first member of the auxiliary specific binding pair. This immobilizes the visible dye at the dye viewing area 52 when flow has occurred. Typically, the first member of the auxiliary specific binding pair is biotin and the second member of the auxiliary specific binding pair is avidin or streptavidin. Other first and second members of the auxiliary specific binding pair can be used. The arrangement of the dye area 50 and the dye viewing area 52 is as described above.

An assay device according to FIG. 1 can be used to detect any analyte that can be detected by a sandwich immunoassay. Among the analytes for which the assay device according to FIG. 1 is particularly suited are the closely related glycoprotein hormones human chorionic gonadotropin (hCG), luteinizing hormone (LH), follicle stimulating hormone (FSH), and thyroid stimulating hormone (TSH). Among other analytes for which the assay device according to FIG. 1 is particularly suited are other protein, polypeptide, and glycoprotein hormones, such as corticotropin-releasing hormone (CRH), growth hormone-releasing hormone (GHRH), prolactin, human growth hormone (hGH), β-lipotropin, corticotropin, β-endorphin, calcitonin, parathormone, human placental lactogen (hPL), insulin, glucagon, pancreatic polypeptide (PP), secretin, cholecystokinin-pancreozymin, motilin, vasoactive intestinal peptide, gastric inhibitory peptide, erythropoietin, and other hormones.

In one preferred alternative, the first and second specific binding partners are non-human monoclonal antibodies, most preferably murine monoclonal antibodies. In this alternative, the sample application zone 34 on the second opposable component 14 preferably contains a fifth specific binding partner as defined above. The fifth specific binding partner is an unlabeled specific binding partner that is specific for human antibodies that bind to the non-human monoclonal antibody. The fifth specific binding partner can be either immobilized or mobile. In this alternative, the first chromatographic medium 16 further includes, in a validation zone 56, a sixth specific binding partner as defined above. The sixth specific binding partner is an immobilized specific binding partner that is specific for human antibodies that bind to the non-human monoclonal antibodies. In this alternative, the presence of detectable label at the validation zone indicates interference in the assay caused by the presence of human-anti-mouse antibodies (HAMA). This detectable label is the second specific binding partner, which is a mobile labeled specific binding partner for the analyte. Typically, in this alternative, the fifth and sixth specific binding partners are mouse immunoglobulin G or a derivative or polymer of mouse immunoglobulin G. For example, although not by way of limitation, the fifth specific binding partner in the sample application zone can be mouse serum as a source of mouse IgG, and the sixth specific binding partner in the validation zone can be a murine monoclonal antibody against α-fetoprotein (AFP). A particularly suitable monoclonal antibody against AFP is an anti-HFP antibody produced by Hybritech (San Diego, Calif.) and designated AFU 212.7. This monoclonal antibody can be replaced by any other murine monoclonal antibody that does not specifically bind to either the analyte or the second specific binding partner.

As an another alternative, when the device detects hCG, the sample application zone can contain, in sample treatment buffer (phosphate buffered saline, pH 7.4, 2% bovine serum albumin, and 4% Triton X-100), 0.5 mg/ml of PolyMAK 33, a heterophilic scavenger antibody (Boehringer Mannheim), 12 μg/ml of monoclonal anti-LH antibody (Hybritech 120119, San Diego, Calif.), and 1 mg/ml of bovine IgG. In this alternative, the fifth specific binding partner is the PolyMAK 33. PolyMAK 33 is a mAb IgG1/F(ab') polymer that efficiently scavenges human anti-mouse antibodies, particularly those specific for IgG1 mouse IgG. The anti-LH antibody is to scavenge luteinizing hormone, which may cross-react with hCG. When the device is to detect one of the related glycoprotein hormones other than hCG, such as LH, TSH, or FSH, the anti-LH antibody is replaced by one or more of anti-hCG antibody, anti-LH antibody, anti-TSH antibody or anti-FSH antibody, depending on the analyte to be detected, in order to minimize cross-reactions. Antibody specific for the analyte to be detected is not included in the sample application zone.

The fifth specific binding partner serves to scavenge any human anti-mouse immunoglobulin G present in the sample. Only if the level of human anti-mouse immunoglobulin G antibodies is so high that the fifth specific binding partner in the sample application zone 34 cannot scavenge the antibodies would detectable label appear at the validation zone 56, thus indicating the presence of interference, such as potential false negative or false positive results, due to HAMA.

When the first and second specific binding partners are murine monoclonal antibodies, a preferred third specific binding partner immobilized at the reference zone is rabbit anti-goat IgG. In this alternative, the fourth specific binding partner in zone 24c is goat IgG, which can be labeled with a label such as colloidal carbon.

Although non-human monoclonal antibodies are used for the first and second specific binding partners in this alternative, the present invention is not limited to the use of non-human monoclonal antibodies for the first and second specific binding partners. Other types of monoclonal antibodies, such as humanized or partially humanized monoclonal antibodies, can be used for these specific binding partners. In a less preferred alternative, it can also be possible to use highly affinity purified polyclonal antibodies for these specific binding partners.

In another preferred alternative, the quantity of third specific binding partner immobilized at the reference zone 32 can be predetermined so that the quantity of fourth specific binding partner that binds to the third specific binding partner at the reference zone 32 gives an intensity of label at the reference zone 32 equivalent to that seen in the detection zone 22 when a predetermined concentration of analyte is present in the sample. Thus, the quantity of third specific binding partner at the reference zone 32 can be preselected so that the intensity of label at the reference zone 32 and the detection zone 22 can be compared, thus giving an indication whether or not the concentration of the analyte to be tested is above or below a clinically important level.

In one preferred alternative, the analyte is hCG. In this alternative, the first specific binding partner is preferably a monoclonal antibody specific for the α-subunit of hCG and the second specific binding partner is preferably a monoclonal antibody specific for the β subunit of hCG and not cross-reactive with luteinizing hormone (LH). In this alternative, a particularly preferred monoclonal antibody specific for the a subunit of hCG is a F(ab')$_2$ fragment of a monoclonal antibody produced by Hybritech (San Diego, Calif.) and designated HCU 061.2. A particularly preferred monoclonal antibody specific for the β subunit of hCG is a monoclonal antibody produced by Hybritech (San Diego, Calif.) and designated HXKG 029.1.3. This arrangement of antibodies can be reversed so that the first specific binding partner is a monoclonal antibody specific for the β subunit of hCG and the second specific binding partner is a monoclonal antibody specific for the α subunit of hCG.

In use, a sample is applied to the sample application zone 34. The first and second opposable components 12 and 14 are then brought into operable contact by closing the device 10. The sample resolubilizes the second specific binding partner in the conjugate pad 24 in zone 24a, as well as the fourth specific binding partner in the conjugate pad 24 in zone 24c. The sample and the resolubilized second specific binding partner are then allowed to migrate through the first chromatographic medium 16, including the detection zone 22 of the first chromatographic medium 16; the sample and the resolubilized fourth specific binding partner are also then allowed to migrate through the second chromatographic medium 26, including the reference zone 32 of the second chromatographic medium 26. As indicated above, the migration of the second specific binding partner is kept substantially separate from the migration of the four specific binding partner. When migration is complete, which can be determined by the appearance of the dye at the dye viewing area 52, the results are viewed through the first aperture 36 for the detection zone 22 and the second aperture 38 for the reference zone 32. The dye viewing area 52 can be viewed through the dye aperture 54. In a positive test, label is present at the detection zone 22 and the reference zone 32. A semi-quantitative determination of the concentration of analyte in the test sample can be made by comparison of the intensity of the label present at the detection zone 22 and at the reference zone 32.

In a valid test, no label is visible at the validation zone 56. If no label appears at the reference zone 32, or if label is visible at the validation zone 56, the assay did not run properly and should be disregarded.

Typically, to achieve results, the assay requires from 30 seconds to 10 minutes, more typically from 1 to 5 minutes, including any period of incubation of the sample on the sample application zone, as well as the time required for chromatography itself. Typically, the assay is performed at room temperature, although it can be performed at 4° C. or up to 37° C. or higher in some cases, depending on the nature of the analyte and the specific binding partners. In some cases, performing the assay at a lower temperature can be desirable to limit degradation, while in other cases, performing the assay at a higher temperature with suitable analytes and specific binding partners can speed up the assay.

2. Device Having One Chromatographic Medium Divided into Functional Zones with Two Labeled Specific Binding Partners In an alternative version of the assay device shown in FIG. 1, one chromatographic medium can be used instead of two chromatographic media. The single chromatographic medium can be divided into two separated functional zones by a conjugate pad. The conjugate pad is located on top of the chromatographic medium and thus is in operable contact with the chromatographic medium between the first and second functional zones. The conjugate pad is itself divided into three portions: a first portion containing, in resolubilizable form, the second specific binding partner, a second portion containing an inert stabilizing medium such as conjugate diluent, and a third portion containing, in resolubilizable form, the fourth specific binding partner, as described above.

Figure 2:
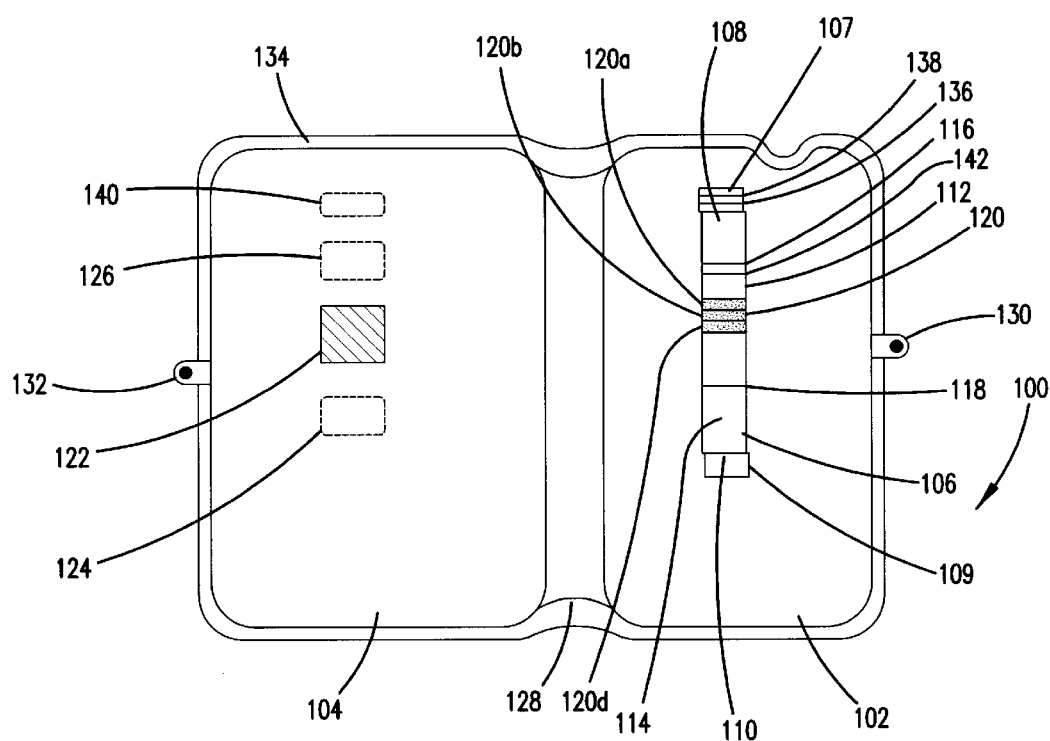
FIG. 2 is a drawing of a second embodiment of an assay device according to the present invention with one chromatographic medium divided into two functional zones and employing two labeled specific binding partners.

This device is shown in FIG. 2. The device 100 has a first opposable component 102 and a second opposable component 104. The first opposable component 102 has a chromatographic medium 106 having a first end 108 and a second end 110. Optionally, the first end 108 of the chromatographic medium 106 is in operable contact with a first absorber 107 and the second end 110 of the chromatographic medium 106 is in operable contact with a second absorber 109. The chromatographic medium 106 is divided into a first functional zone 112 and a second functional zone 114. The first functional zone 112 has a detection zone 116 as described above with the first specific binding partner, which is an unlabeled, immobilized specific binding partner for the analyte. The second functional zone 114 has a reference zone 118 as described above with the third specific binding partner, which binds the labeled fourth specific binding partner, as described above, but does not bind the analyte or a labeled specific binding partner to the analyte. The third specific binding partner is other than the analyte or an analyte analogue. A conjugate pad 120 is placed in operable contact with the chromatographic medium 106 between the first functional zone 112 and the second functional zone 114 so that it divides the first functional zone 112 from the second functional zone 114. Typically, the conjugate pad 120 is placed over the chromatographic medium 106 overlapping both the first functional zone 112 and the second functional zone 114. The first functional zone 112 and the second functional zone 114 can be separated by a portion of the chromatographic medium 106 that is directly under the middle portion of the conjugate pad 120. The conjugate pad 120 has three portions, as described above: a first portion 120a containing the second specific binding partner, a second portion 120b containing an inert stabilizing medium such as conjugate diluent, and a third portion 120c containing the fourth specific binding partner. The first portion 120a and the third portion 120c are functionally isolated so that when a liquid is added to the conjugate pad 120, the second specific binding partner in the first portion 120a migrates substantially only into the first functional zone 112, and the fourth specific binding partner in the third portion 120c migrates substantially only into the second functional zone 114. As used herein, the term "two functional zones" does not exclude the use of more than two functional zones in a device constructed substantially according to these principles.

The second opposable component 104 has a sample application zone 122. The second opposable component 104 also includes a first aperture 124 and a second aperture 126. The first aperture 124 is for viewing of the detection zone 116 and the second aperture 126 is for viewing of the reference zone 118. The device 100 also includes a hinge 128 joining the first opposable component 102 and the second opposable component 104, as well as engagers such as locks 130 and 132 and a gasket 134. Alternatively, the locks can be replaced by an adhesive strip as described above.

Preferably, the chromatographic medium 106 has a dye area 136 and a dye viewing area 138. The dye area 136 and the dye viewing area 138 can be located in the first absorber 107 as described above. Alternatively, the dye area 136 and the dye viewing area 138 can be located adjacent to the first end 108 of the chromatographic medium 106, with the dye viewing area 138 being located closer to the first end 108 than the dye area 136. Migration of the sample and the resolubilized labeled second specific binding partner within the chromatographic medium 106 causes the dye to migrate from the dye area 136 to the dye viewing area 138, located as described above. When the dye reaches the dye viewing area 138, it is visible through a dye aperture 140 on the second opposable component 104. This serves as a visible signal to indicate that flow has occurred and that the assay can be read and interpreted.

In an alternative, the dye area 136 contains a resolubilizable visible dye linked to a first member of an auxiliary specific binding pair that does not bind to any other specific binding partner in the device or to the analyte, and the dye viewing area 138 contains an immobilized second member of the auxiliary specific binding pair that binds only the first member of the auxiliary specific binding pair. This immobilizes the visible dye at the dye viewing area 138 when flow has occurred. Typically, the first member of the auxiliary specific binding pair is biotin and the second member of the auxiliary specific binding pair is avidin or streptavidin. Other first and second members of the auxiliary specific binding pair can be used. The dye area 136 and the dye viewing area 138 are located as described above.

Preferably, when the first and second specific binding partners are non-human monoclonal antibodies, the chromatographic medium 106 also contains, in the first zone 112, a validation zone 142 as described above.

The device of FIG. 2 is used exactly as the device of FIG. 1, with the sample being placed on the sample application zone 122 on the second opposable component 104 and the first and second opposable components 102 and 104 being brought into operable contact to apply the sample to the conjugate pad 120. The sample and the resolubilized second specific binding partner then migrate through the first functional zone 112 of the chromatographic medium 106; the sample and the resolubilized fourth specific binding partner also then migrate through the second functional zone 114 of the chromatographic medium 106. The assay is read exactly as the device of FIG. 1.

3. Device Having Two Chromatographic Media and Conjugate Pad with One Labeled Specific Binding Partner In another alternative, another embodiment of a device according to the present invention has two chromatographic media, but uses a single labeled specific binding partner. This embodiment is shown in FIG. 3.

For convenience in referring to them below, the specific binding partners used in this embodiment, including optional specific binding partners, are recited below:

The first specific binding partner is an immobilized, unlabeled, specific binding partner that binds the analyte, located in a detection zone. The second specific binding partner is a mobile labeled specific binding partner for the analyte located in a conjugate pad. The third specific binding partner is an immobilized, unlabeled specific binding partner, other than the analyte or an analyte analogue, that is located in a reference zone and that does not bind the analyte, but does bind the second specific binding partner. The fourth specific binding partner, whose use is optional but preferable, is located in a sample application zone and is unlabeled; it is specific for human antibodies that bind the second specific binding partner. Typically, when the second specific binding partner is a non-human monoclonal antibody as described further below, the fourth specific binding partner is specific for human antibodies that bind to the non-human monoclonal antibody. The fourth specific binding partner can be immobilized or mobile. The fifth specific binding partner is optional and is used along with the fourth specific binding partner; it is unlabeled, immobilized in a validation zone, and is also specific for human antibodies that bind the second specific binding partner, typically a non-human monoclonal antibody as described further below.

Figure 3:
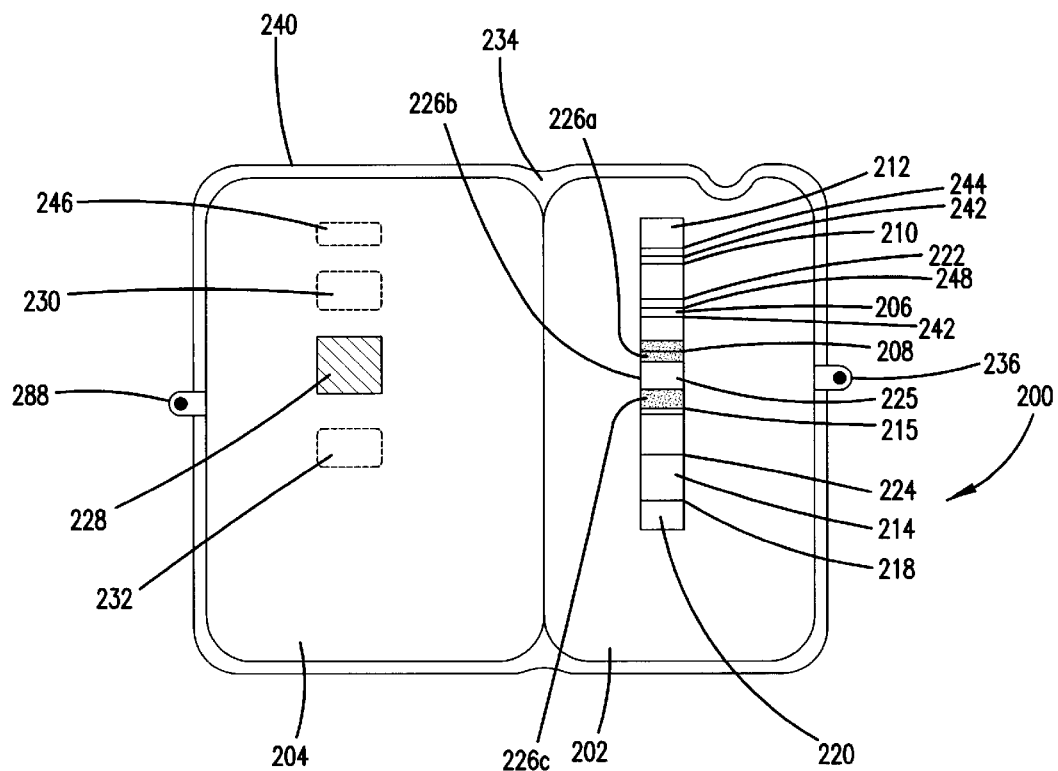
FIG. 3 is a drawing of a third embodiment of an assay device according to the present invention with two chromatographic media and employing one labeled specific binding partner.

This device is shown in FIG. 3. The device 200 has a first opposable component 202 and a second opposable component 204. The first opposable component 202 has a first chromatographic medium 206 with a first end 208 and a second end 210. Optionally, the second end 210 of the first chromatographic medium 206 is in operable contact with a first absorber 212. The first opposable component 202 also has a second chromatographic medium 214 with a first end 216 and a second end 218. Optionally, the second end 218 of the second chromatographic medium 214 is in operable contact with a second absorber 220. The first chromatographic medium 206 has a detection zone 222 containing the first specific binding partner. The first specific binding partner is an immobilized specific binding partner for the analyte as described above. The second chromatographic medium 214 has a reference zone 224 containing the third specific binding partner, which is other than the analyte or an analyte analogue. The third specific binding partner, as described above, binds the second specific binding partner which is a mobile labeled specific binding partner for the analyte. The third specific binding partner does not bind the analyte.

The first opposable component 202 also includes a conjugate pad 226. The conjugate pad 226 has three portions: a first portion 226a, a second portion 226b, and a third portion 226c. The first and third portions 226a and 226c have the second specific binding partner, which is a mobile labeled specific binding partner for the analyte. The second portion 226b, which separates the first and third portions 226a and 226c, has an inert stabilizing medium such as conjugate diluent. The first portion 226a and the third portion 226c are functionally isolated as described above so that the resolubilized second specific binding partner in the first portion 226a migrates substantially only through the first chromatographic medium 206 and the resolubilized second specific binding partner in the third portion 226c migrates substantially only through the second chromatographic medium 214.

The second opposable component 206 includes a sample application zone 228. The second opposable component 206 also includes a first aperture 230 for viewing of the detection zone 222 and a second aperture 232 for viewing of the reference zone 224. The first and second opposable components 202 and 204 are joined by a hinge 234.

The first and second opposable components 202 and 204 preferably further comprise engagers that secure the first and second opposable components 202 and 204 in opposition or operable contact. The engagers can comprise locks, such as locks 236 and 238, that are engaged when the first opposable component 202 and the second opposable component 204 are brought into opposition. The construction and dimensions of the locks 236 and 238 can be varied to exert the optimal degree of pressure on the first and second opposable components 202 and 204. The degree of pressure that is optimal can depend on the thickness of construction of the first chromatographic medium 206, the second chromatographic medium 214, the intended sample volume, and other factors. Alternatively, the first and second opposable components 202 and 204 can be held in position by means of an adhesive strip that is applied to one of the first or second opposable components 202 and 204; the adhesive strip can be provided with a release liner. To guard against leakage of samples or reagents, a sealing ridge or gasket 240 can be positioned around the perimeter of the first and second opposable components 202 and 204. Although the use of the engagers, such as locks 236 and 238 or, alternatively, the adhesive strip, and the use of the sealing ridge or gasket 240, is generally preferred, these elements are not necessary to construct a basic device according to the present invention.

Alternatively, the opposable components can be incorporated into a housing with a bevel closure, such as that disclosed in U.S. Pat. No. 5,441,698 to Norell, incorporated herein, as described above.

In one particularly preferred alternative of the device according to the present invention, the first absorber 212 further includes a dye area 242 and a dye viewing area 244 as described above. In another alternative, the first chromatographic medium 206 further includes the dye area 242 between the detection zone 222 and the second end 210 of the first chromatographic medium 206. The dye area 242 has a resolubilizable visible dye. During the performance of the assay, the dye in the dye area 242 is resolubilized and migrates from the dye area 242 to the dye viewing area 244. In this alternative, the second opposable component 204 further includes a dye aperture 246 allowing viewing of the dye viewing area 244 located as described above. The dye aperture 246 on the second opposable component 204 is located so that the dye area 242 on the first opposable component 202 is not visible before migration of the dye has occurred from the dye area 242 to the dye viewing area 244. This gives a visual indication that flow through the first chromatographic medium 206 has occurred and that the assay can be read and interpreted.

In another alternative, the dye area 242 contains a visible dye linked to a first member of an auxiliary specific binding pair that does not bind to any other specific binding partner in the device or to the analyte, and the dye viewing area 244 contains an immobilized second member of the auxiliary specific binding pair that binds only the first member of the auxiliary specific binding pair. This immobilizes the visible dye at the dye viewing area 242 when flow has occurred. Typically, the first member of the auxiliary specific binding pair is biotin and the second member of the auxiliary specific binding pair is avidin or streptavidin. Other first and second members of the auxiliary specific binding pair can be used. In this alternative, the dye area 242 and the dye viewing area 244 are located as described above.

An assay device according to FIG. 3 can be used to detect any analyte that can be detected by a sandwich immunoassay, as described above. Among the analytes for which the assay device according to FIG. 3 is particularly suited are the closely related glycoprotein hormones human chorionic gonadotropin (hCG), luteinizing hormone (LH), follicle stimulating hormone (FSH), and thyroid stimulating hormone (TSH). Among other analytes for which the assay device according to FIG. 3 is particularly suited are other protein, polypeptide, and glycoprotein hormones as recited above.

In one preferred alternative, the first and second specific binding partners are non-human monoclonal antibodies, most preferably murine monoclonal antibodies. In this alternative, the sample application zone 228 on the second opposable component 204 preferably contains a fourth specific binding partner as defined above. The fourth specific binding partner is an unlabeled specific binding partner that is specific for human antibodies that bind to the non-human monoclonal antibody. The fourth specific binding partner can be either immobilized in the sample application zone 228 or mobile and located in the sample application zone 228. In this alternative, the first chromatographic medium 206 further includes, in a validation zone 248, a fifth specific binding partner as defined above. The fifth specific binding partner is an immobilized specific binding partner that is specific for human antibodies that bind to the non-human monoclonal antibodies. In this alternative, the presence of detectable label at the validation zone 248 indicates interference in the assay caused by the presence of human-anti-mouse antibodies (HAMA). This detectable label is the second specific binding partner, which is a mobile labeled specific binding partner for the analyte. Typically, in this alternative, the fourth and fifth specific binding partners are mouse immunoglobulin G or a derivative or polymer of mouse immunoglobulin G, as described above. For example, although not by way of limitation, the fourth specific binding partner in the sample application zone can be mouse serum as a source of mouse IgG, and the fifth specific binding partner in the validation zone can be a murine monoclonal antibody against x-fetoprotein (AFP), as described above.

As an another alternative, when the device detects hCG, the sample application zone 228 can contain, in sample treatment buffer (phosphate buffered saline, pH 7.4, 2% bovine serum albumin, and 4% Triton X-100), 0.5 mg/ml of PolyMAK 33, a heterophilic scavenger antibody (Boehringer Mannheim), 12 µg/ml of monoclonal anti-LH antibody (Hybritech 120119, San Diego, Calif.), and 1 mg/ml of bovine IgG, as described above.

The fourth specific binding partner serves to scavenge any human anti-mouse immunoglobulin G present in the sample. Only if the level of human anti-mouse immunoglobulin G antibodies is so high that the fourth specific binding partner in the sample application zone 228 cannot scavenge the antibodies would detectable label appear at the validation zone 248, thus indicating the presence of interference due to HAMA.

When the first and second specific binding partners are murine monoclonal antibodies, a preferred third specific binding partner immobilized at the reference zone 224 is goat anti-mouse IgG. In this alternative, when the analyte is hCG, the second specific binding partner in zones 226a and 226c can be a monoclonal antibody to the β subunit of hCG, which can be labeled with a label such as colloidal carbon.

In another preferred alternative, the quantity of third specific binding partner immobilized at the reference zone 224 can be predetermined so that the quantity of second specific binding partner that binds to the third specific binding partner at the reference zone 224 gives an intensity of label at the reference zone 224 equivalent to that seen in the detection zone 222 when a predetermined concentration of analyte is present in the sample, as described above.

In one preferred alternative, the analyte is hCG. In this alternative, the first specific binding partner is preferably a monoclonal antibody specific for the x-subunit of hCG and the second specific binding partner is preferably a monoclonal antibody specific for the a subunit of hCG and not cross-reactive with luteinizing hormone (LH). Particularly preferred monoclonal antibodies for this analyte are described above. Other arrangements of first and second specific binding partners are possible: for example, the first specific binding partner can be specific for the β subunit of hCG and the second specific binding partner can be specific for the a subunit of hCG.

As described above, an assay device according to FIG. 3 can be constructed to assay hormones such as TSH, FSH, or LH instead of hCG.

4. Device Having One Chromatographic Medium Divided into Functional Zones with One Labeled Specific Binding Partner Another embodiment of an assay device according to the present invention employs one chromatographic medium divided into functional zones and one labeled specific binding partner, which is bound at both the reference zone and the detection zone. Thus, this device embodies features of the devices shown in FIGS. 2 and 3 in a new combination. The specific binding partners employed in this embodiment of the device are the same as those of the device of FIG. 3.

Figure 4:
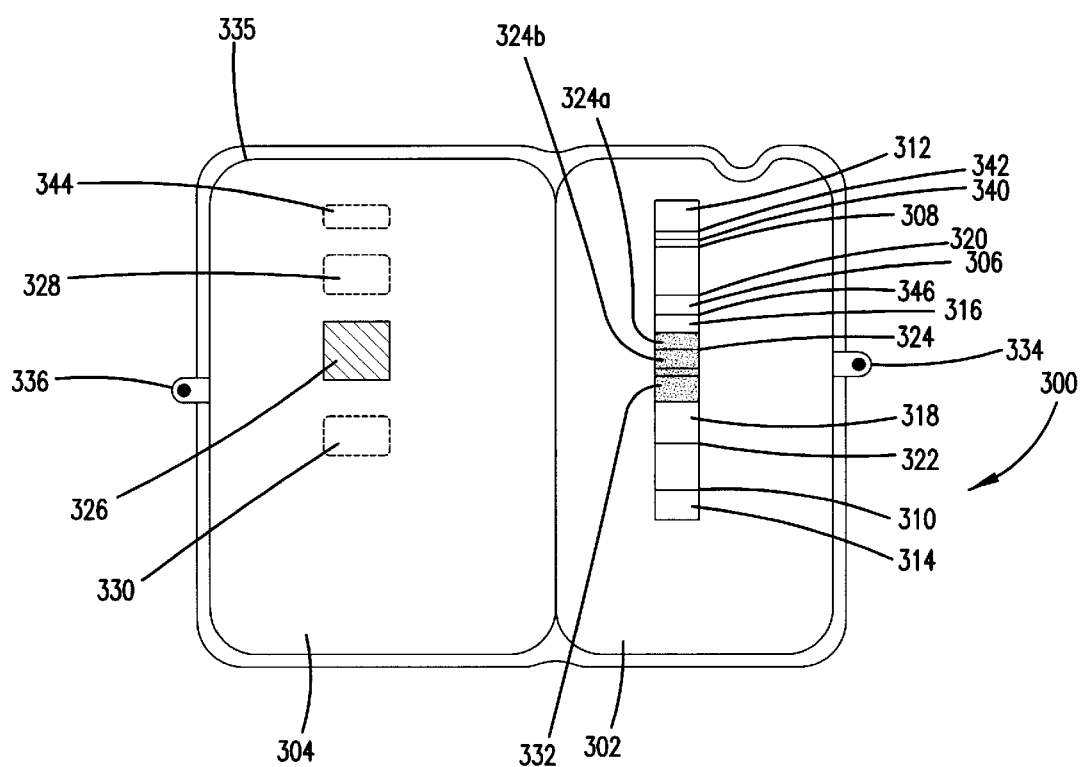
FIG. 4 is a drawing of a fourth embodiment of an assay device according to the present invention with one chromatographic medium divided into two functional zones and employing one labeled specific binding partner.

This device is shown in FIG. 4. The device 300 has a first opposable component 302 and a second opposable component 304. The first opposable component 302 has a chromatographic medium 306 having a first end 308 and a second end 310. Optionally, the first end 308 of the chromatographic medium 306 is in operable contact with a first absorber 312 and the second end 310 of the chromatographic medium 306 is in operable contact with a second absorber 314. The chromatographic medium 306 is divided into a first functional zone 316 and a second functional zone 318. The first functional zone 316 has a detection zone 320 as described above. The detection zone 320 contains the first specific binding partner. The second functional zone 318 has a reference zone 322 as described above with the third specific binding partner. The third specific binding partner, which is other than the analyte or an analyte analogue, binds the labeled second specific binding partner, as described above, but does not bind the analyte or a labeled specific binding partner to the analyte. A conjugate pad 324 is placed in operable contact with the chromatographic medium 306 between the first functional zone 316 and the second functional zone 318 so that the conjugate pad 324 divides the first functional zone 316 from the second functional zone 318, as described above for the device of FIG. 2. Typically, the conjugate pad 324 is placed on top of the chromatographic medium 306. The conjugate pad 324 has three portions, as described above: a first portion 324a containing the second specific binding partner, a second portion 324b containing an inert stabilizing medium such as conjugate diluent, and a third portion 324c also containing the second specific binding partner. The first portion 324a and the third portion 324c are functionally isolated as described above so that the resolubilized second specific binding partner in the first portion 324a migrates substantially only through the first functional zone 316 and the resolubilized second specific binding partner in the third portion 324c migrates substantially only through the second functional zone 318.

The second opposable component 304 includes a sample application zone 326. The second opposable component 304 also includes a first aperture 328 for viewing of the detection zone 320 and a second aperture 330 for viewing of the reference zone 322. The first and second opposable components 302 and 304 are joined by a hinge 332.

The first and second opposable components 302 and 304 preferably further comprise engagers that secure the first and second opposable components 302 and 304 in opposition or operable contact. The engagers can comprise locks, such as locks 334 and 336, as described above. Alternatively, the first and second opposable components 302 and 304 can be held in position by means of an adhesive strip that is applied to one of the first or second opposable components 302 and 304 as described above. To guard against leakage of samples or reagents, a sealing ridge or gasket 338 can be positioned around the perimeter of the first and second opposable components 302 and 304. Although the use of the engagers, such as locks 334 and 336 or, alternatively, the adhesive strip, and the use of the sealing ridge or gasket 338, is generally preferred, these elements are not necessary to construct a basic device according to the present invention.

Alternatively, the opposable components can be incorporated into a housing with a bevel closure, such as that disclosed in U.S. Pat. No. 5,441,698 to Norell, incorporated herein, as described above.

In one particularly preferred alternative of the device according to the present invention, the chromatographic medium 306 further includes a dye area 340 and a dye viewing area 342. The dye area 340 and the dye viewing area 342 can be located in the first absorber 312. Alternatively, the dye area 340 and the dye viewing area 342 can be located between the detection zone 320 and the first end 308 of the chromatographic medium 306. The dye area 340 has a resolubilizable visible dye. During the performance of the assay, the dye in the dye area 340 is resolubilized and migrates from the dye area 340 to the dye viewing area 342. In this alternative, the second opposable component 304 further includes a dye aperture 344 allowing viewing of the dye viewing area 342 on the first opposable component 302. The dye aperture 344 on the second opposable component 304 is located so that the dye area 340 on the first opposable component 302 is not visible before migration of the dye has occurred from the dye area 340 to the dye viewing area 342. This gives a visual indication that flow through the chromatographic medium 306 has occurred and that the assay can be read and interpreted.

In an alternative, the dye area 340 contains a visible dye linked to a first member of an auxiliary specific binding pair that does not bind to any other specific binding partner in the device or to the analyte, and the dye viewing area 342 contains an immobilized second member of the auxiliary specific binding pair that binds only the first member of the auxiliary specific binding pair. This immobilizes the visible dye at the dye viewing area 342 when flow has occurred. Typically, the first member of the auxiliary specific binding pair is biotin and the second member of the auxiliary specific binding pair is avidin or streptavidin. Other first and second members of the auxiliary specific binding pair can be used. In this alternative, the dye area 340 and the dye viewing area 342 are located as described above.

An assay device according to FIG. 4 can be used to detect any analyte that can be detected by a sandwich immunoassay, as described above.

In one preferred alternative, the first and second specific binding partners are non-human monoclonal antibodies, most preferably murine monoclonal antibodies. In this alternative, the sample application zone 326 on the second opposable component 304 preferably contains a fourth specific binding partner as defined above. The fourth specific binding partner is an unlabeled specific binding partner that is specific for human antibodies that bind to the non-human monoclonal antibody. The fourth specific binding partner can be immobilized or mobile. In this alternative, the chromatographic medium 306 further includes, in a validation zone 346, a fifth specific binding partner as defined above. The fifth specific binding partner is an immobilized specific binding partner that is specific for human antibodies that bind to the non-human monoclonal antibodies. In this alternative, the presence of detectable label at the validation zone 346 indicates interference, such as the possible occurrence of false negatives or false positives, in the assay caused by the presence of human-anti-mouse antibodies (HAMA). This detectable label is the second specific binding partner, which is a mobile labeled specific binding partner for the analyte. Typically, in this alternative, the fourth and fifth specific binding partners are mouse immunoglobulin G or a derivative or polymer of mouse immunoglobulin G, as described above.

As an another alternative, when the device detects hCG, the sample application zone 326 can contain, in sample treatment buffer (phosphate buffered saline, pH 7.4, 2% bovine serum albumin, and 4% Triton X-100), 0.5 mg/ml of PolyMAK 33, a heterophilic scavenger antibody (Boehringer Mannheim), 12 µg/ml of monoclonal anti-LH antibody (Hybritech 120119, San Diego, Calif.), and 1 mg/ml of bovine IgG, as described above.

The fourth specific binding partner serves to scavenge any human anti-mouse immunoglobulin G present in the sample. Only if the level of human anti-mouse immunoglobulin G antibodies is so high that the fifth specific binding partner in the sample application zone 326 cannot scavenge the antibodies would detectable label appear at the validation zone 346, thus indicating the presence of interference due to HAMA.

When the first and second specific binding partners are murine monoclonal antibodies, a preferred third specific binding partner immobilized at the reference zone 322 is goat anti-mouse IgG. In this alternative, when the analyte is hCG, the second specific binding partner in zones 324a and 324c can be a monoclonal antibody to the β subunit of hCG, which can be labeled with a label such as colloidal carbon.

In another preferred alternative, the quantity of third specific binding partner immobilized at the reference zone 322 can be predetermined so that the quantity of second specific binding partner that binds to the third specific binding partner at the reference zone 322 gives an intensity of label at the reference zone 322 equivalent to that seen in the detection zone 320 when a predetermined concentration of analyte is present in the sample, as described above.

In one preferred alternative, the analyte is hCG. In this alternative, the first specific binding partner is preferably a monoclonal antibody specific for the α-subunit of hCG and the second specific binding partner is preferably a monoclonal antibody specific for the β subunit of hCG and not cross-reactive with luteinizing hormone (LH). Particularly preferred monoclonal antibodies for this analyte are described above. Other alternative combinations for the first and second specific binding partners can be used as described above; for example, the first specific binding partner can be a monoclonal antibody specific for the β subunit of hCG and the second specific binding partner can be a monoclonal antibody specific for the α subunit of hCG.

As described above, an assay device according to FIG. 4 can be constructed to assay hormones such as TSH, FSH, or LH instead of hCG.

5. Device Having Two Chromatographic Media, On-Board Control, and Conjugate Pad with One Labeled Specific Binding Partner Another embodiment of an assay device according to the present invention is a device having two chromatographic media, an on-board control, and a conjugate pad with a single labeled specific binding partner. The on-board control eliminates the need for external controls. Additionally, the on-board control functions as a true control to ensure that what is measured is identical to the analyte.

For convenience in referring to them below, the specific binding partners used in this embodiment, including optional specific binding partners, are recited below:

The first specific binding partner is an immobilized, unlabeled, specific binding partner that binds the analyte, located in a detection zone. The second specific binding partner is a mobile labeled specific binding partner for the analyte located in a conjugate pad. The third specific binding partner, whose use is optional but preferable, is located in a sample application zone and is and unlabeled; it is specific for human antibodies that bind the second specific binding partner. Typically, the second specific binding partner is a non-human monoclonal antibody as described further below and the third specific binding partner is specific for human antibodies that bind to the non-human monoclonal antibody. The third specific binding partner can be immobilized or mobile. The fourth specific binding partner is optional and is used along with the third specific binding partner; it is unlabeled, immobilized in a validation zone, and is also specific for human antibodies that bind the second specific binding partner, typically, a non-human monoclonal antibody as described further below.

The device further employs an analyte or analyte analogue immobilized at a control zone. The analyte or analyte analogue binds the labeled second specific binding partner.

Figure 5:
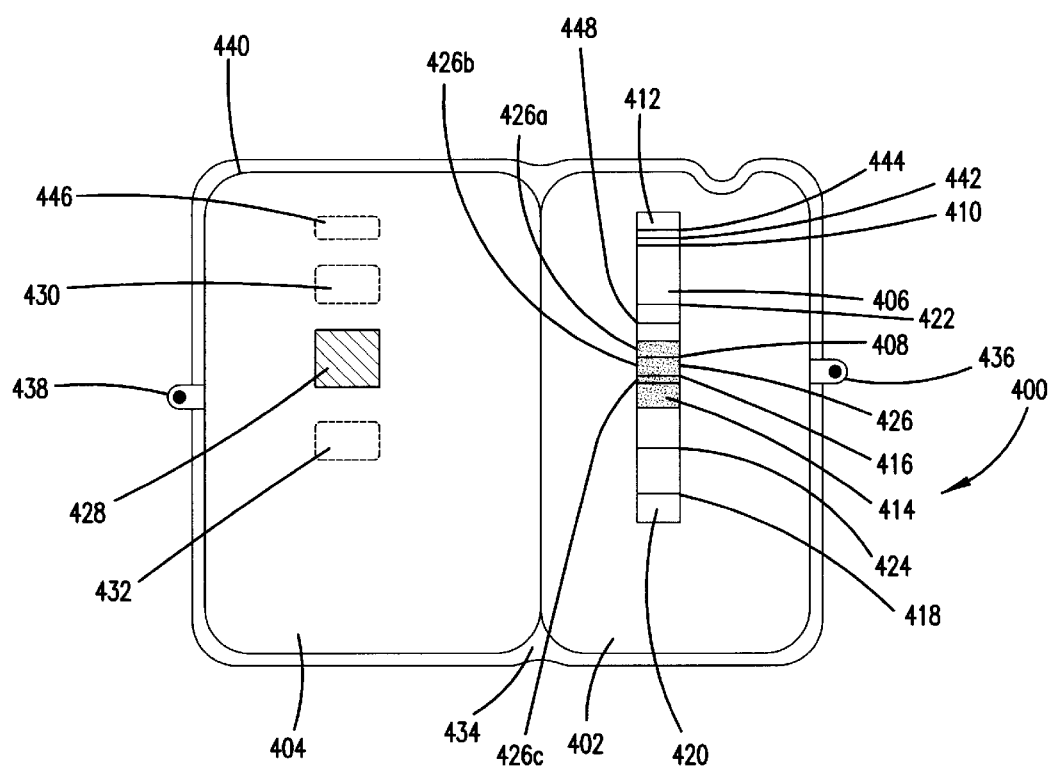
FIG. 5 is a drawing of a fifth embodiment of an assay device according to the present invention with two chromatographic media and employing one labeled specific binding partner, with an on-board control of immobilized analyte or analyte analogue.

This device is shown in FIG. 5. The device 400 has a first opposable component 402 and a second opposable component 404. The first opposable component 402 has a first chromatographic medium 406 with a first end 408 and a second end 410. Optionally, the second end 410 of the first chromatographic medium 406 is in operable contact with a first absorber 412. The first opposable component 402 also has a second chromatographic medium 414 with a first end 416 and a second end 418. Optionally, the second end 418 of the second chromatographic medium 414 is in operable contact with a second absorber 420. The first chromatographic medium 406 has a detection zone 422 containing the first specific binding partner. The first specific binding partner is an immobilized specific binding partner for the analyte as described above. The second chromatographic medium 414 has a control zone 424 containing the immobilized analyte or analyte analogue.

The first opposable component 402 also includes a conjugate pad 426 in operable contact with both the first chromatographic medium 406 and the second chromatographic medium 414. The conjugate pad 426 has three portions: a first portion 426a, a second portion 426b, and a third portion 426c. The first and third portions 426a and 426c have the second specific binding partner, which is a mobile labeled specific binding partner for the analyte. The second portion 426b, which separates the first and third portions 426a and 426c, has an inert stabilizing medium such as conjugate diluent. The first portion 426a and the third portion 426c are functionally isolated as described above so that the resolubilized second specific binding partner in the first portion 426a migrates substantially only through the first chromatographic medium 406 and the resolubilized second specific binding partner in the third portion 426c migrates substantially only through the second chromatographic medium 414.

The second opposable component 404 includes a sample application zone 428. The second opposable component 404 also includes a first aperture 430 for viewing of the detection zone 422 and a second aperture 432 for viewing of the control zone 424. The first and second opposable components 402 and 404 are joined by a hinge 434.

The first and second opposable components 402 and 404 preferably further comprise engagers that secure the first and second opposable components 402 and 404 in opposition or operable contact. The engagers can comprise locks, such as locks 436 and 438, as described above, or, alternatively, the first and second opposable components 402 and 404 can be held in position by means of an adhesive strip that is applied to one of the first or second opposable components 402 and 404; the adhesive strip can be provided with a release liner. To guard against leakage of samples or reagents, a sealing ridge or gasket 440 can be positioned around the perimeter of the first and second opposable components 402 and 404. Although the use of the engagers, such as locks 436 and 438 or, alternatively, the adhesive strip, and the use of the sealing ridge or gasket 440, is generally preferred, these elements are not necessary to construct a basic device according to the present invention.

Alternatively, the opposable components can be incorporated into a housing with a bevel closure, such as that disclosed in U.S. Pat. No. 5,441,698 to Norell, incorporated herein, as described above.

In one particularly preferred alternative of the device according to the present invention, the first chromatographic medium 406 further includes a dye area 442 and a dye viewing area 444. The dye area 442 and the dye viewing area 444 can be located in the first absorber 412 as described above. Alternatively, the dye area 442 and the dye viewing area 444 can be located between the detection zone 422 and the second end 410 of the first chromatographic medium 406. The dye area 442 has a resolubilizable visible dye. During the performance of the assay, the dye in the dye area 442 is resolubilized and migrates from the dye area 442 to the dye viewing area 444. In this alternative, the second opposable component 404 further includes a dye aperture 446 allowing viewing of the dye viewing area 444 on the first opposable component 402. The dye aperture 446 on the second opposable component 404 is located so that the dye area 442 on the first opposable component 402 is not visible before migration of the dye has occurred from the dye area 442 to the dye viewing area 444. This gives a visual indication that flow through the first chromatographic medium 406 has occurred and that the assay can be read and interpreted.

In an alternative, the dye area 442 contains a visible dye linked to a first member of an auxiliary specific binding pair that does not bind to any other specific binding partner in the device or to the analyte, and the dye viewing area 444 contains an immobilized second member of the auxiliary specific binding pair that binds only the first member of the auxiliary specific binding pair. This immobilizes the visible dye at the dye viewing area 444 when flow has occurred. Typically, the first member of the auxiliary specific binding pair is biotin and the second member of the auxiliary specific binding pair is avidin or streptavidin. Other first and second members of the auxiliary specific binding pair can be used. In this alternative, the dye area 442 and the dye viewing area 444 are located as described above.

In another preferred alternative, the quantity of analyte or analyte analogue immobilized at the control zone 424 can be predetermined so that the quantity of labeled second specific binding partner that binds to the analyte or analyte analogue at the control zone 424 gives an intensity of label at the control zone 424 equivalent to that seen in the detection zone 422 when a predetermined concentration of analyte is present in the sample. Thus, the quantity of analyte or analyte analogue at the control zone 424 can be preselected so that the intensity of label at the control zone 424 and the detection zone 422 can be compared, thus giving an indication whether or not the concentration of the analyte to be tested is above or below a clinically important level.

An assay device according to FIG. 5 can be used to detect any analyte that can be detected by a sandwich immunoassay, as described above.

In one preferred alternative, the first and second specific binding partners are non-human monoclonal antibodies, most preferably murine monoclonal antibodies. In this alternative, the sample application zone 428 on the second opposable component 404 preferably contains a third specific binding partner as defined above. The third specific binding partner is an unlabeled specific binding partner that is specific for human antibodies that bind to the non-human monoclonal antibody. The third specific binding partner can be immobilized or mobile. In this alternative, the first chromatographic medium 406 further includes, in a validation zone 448, a fourth specific binding partner as defined above. The fourth specific binding partner is an immobilized specific binding partner that is specific for human antibodies that bind to the non-human monoclonal antibodies. In this alternative, the presence of detectable label at the validation zone 448 indicates interference in the assay caused by the presence of human-anti-mouse antibodies (HAMA). This detectable label is the second specific binding partner, which is a mobile labeled specific binding partner for the analyte. The third specific binding partner serves to scavenge any human anti-mouse immunoglobulin G present in the sample. Only if the level of human anti-mouse immunoglobulin G antibodies is so high that the third specific binding partner in the sample application zone 428 cannot scavenge the antibodies would detectable label appear at the validation zone 448, thus indicating the presence of interference due to HAMA. Preferred examples of third and fourth specific binding partners are described above.

In one preferred alternative, the analyte is hCG. In this alternative, the first specific binding partner is preferably a monoclonal antibody specific for the a-subunit of hCG and the second specific binding partner is preferably a monoclonal antibody specific for the β subunit of hCG and not cross-reactive with luteinizing hormone (LH). Particularly preferred monoclonal antibodies for this analyte are described above.

As described above, an assay device according to FIG. 5 can be constructed to assay hormones such as TSH, FSH, or LH instead of hCG.

6. Device Having One Chromatographic Medium, On-Board Control, and Conjugate Pad with One Labeled Specific Binding Partner Another embodiment of an assay device according to the present invention has one chromatographic medium divided into two functional zones and one labeled specific binding partner, like the device shown in FIG. 4, but has an on-board control, like the device shown in FIG. 5. This device is shown in FIG. 6.

The specific binding partners used in this embodiment are the same as those used in the device of FIG. 5.

Figure 6:
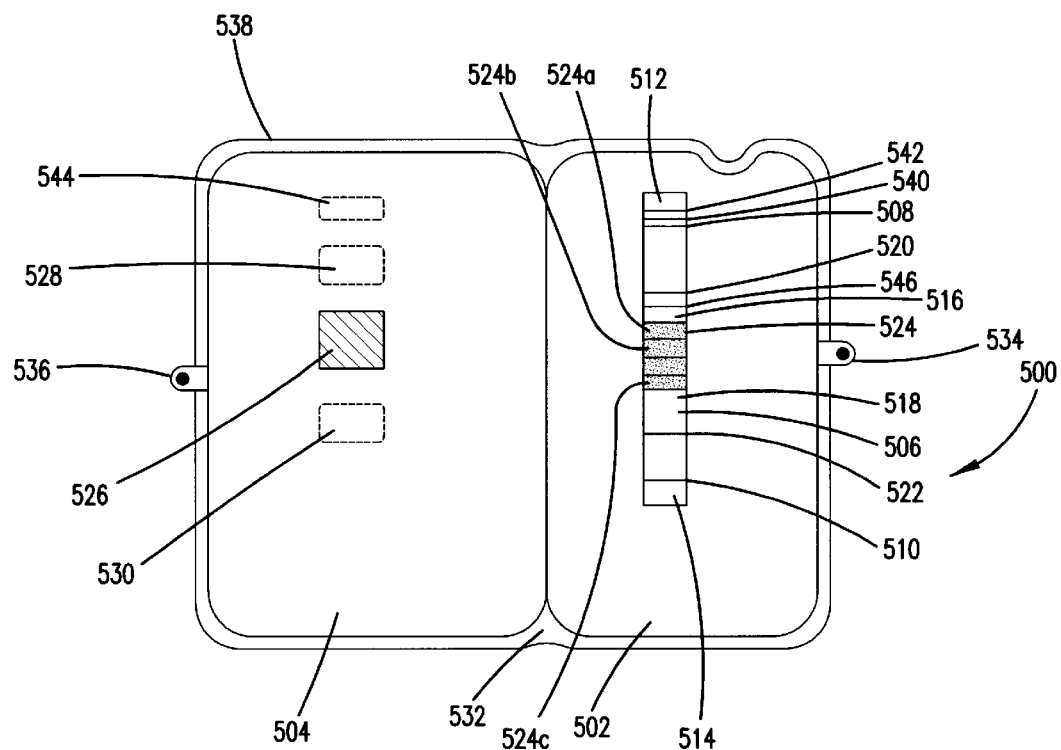
FIG. 6 is a drawing of a sixth embodiment of an assay device according to the present invention with one chromatographic medium divided into two functional zones and employing one labeled specific binding partner, with an on-board control of immobilized analyte or analyte analogue.

This device is shown in FIG. 6. The device 500 has a first opposable component 502 and a second opposable component 504. The first opposable component 502 has a chromatographic medium 506 having a first end 508 and a second end 510. Optionally, the first end 508 of the chromatographic medium 506 is in operable contact with a first absorber 512 and the second end 510 of the chromatographic medium 506 is in operable contact with a second absorber 514. The chromatographic medium 506 is divided into a first functional zone 516 and a second functional zone 518. The first functional zone 516 has a detection zone 520 as described above. The detection zone 520 contains the first specific binding partner. The second functional zone 518 has a control zone 522 as described above with an analyte or analyte analogue immobilized at the control zone. A conjugate pad 524 is placed in operable contact with the chromatographic medium 506, including the first functional zone 516 and the second functional zone 518 so that the conjugate pad 524 divides the first functional zone 516 from the second functional zone 518 as described above for the device of FIG. 2. The conjugate pad 524 has three portions, as described above: a first portion 524a containing the second specific binding partner, a second portion 524b containing an inert stabilizing medium such as conjugate diluent, and a third portion 524c also containing the second specific binding partner. The first portion 524a and the third portion 524c are functionally separated as described above so that the resolubilized second specific binding partner in the first portion 524a migrates substantially only through the first functional zone 516 and the resolubilized second specific binding partner in the third portion 524c migrates substantially only through the second functional zone 518.

The second opposable component 504 includes a sample application zone 526. The second opposable component 504 also includes a first aperture 528 for viewing of the detection zone 520 and a second aperture 530 for viewing of the control zone 522. The first and second opposable components 502 and 504 are joined by a hinge 532.

The first and second opposable components 502 and 504 preferably further comprise engagers that secure the first and second opposable components 502 and 504 in opposition or operable contact. The engagers can comprise locks, such as locks 534 and 536, as described above, or an adhesive strip. To guard against leakage of samples or reagents, a sealing ridge or gasket 538 can be positioned around the perimeter of the first and second opposable components 502 and 504. Although the use of the engagers, such as locks 534 and 536 or, alternatively, the adhesive strip, and the use of the sealing ridge or gasket 538, is generally preferred, these elements are not necessary to construct a basic device according to the present invention.

Alternatively, the opposable components can be incorporated into a housing with a bevel closure, such as that disclosed in U.S. Pat. No. 5,441,698 to Norell, incorporated herein, as described above.

In one particularly preferred alternative of the device according to the present invention, the chromatographic medium 506 further includes a dye area 540 and a dye viewing area 542. The dye area 540 and the dye viewing area 542 can be located in the first absorber 512. Alternatively, the dye area 540 and the dye viewing area 542 can be located between the detection zone 520 and the first end 508 of the chromatographic medium 506. The dye area 540 has a resolubilizable visible dye. During the performance of the assay, the dye in the dye area 540 is resolubilized and migrates from the dye area 540 to the dye viewing area 542. In this alternative, the second opposable component 504 further includes a dye aperture 544 allowing viewing of the dye viewing area 542 on the first opposable component 502. The dye aperture 544 on the second opposable component 504 is located so that the dye area 540 on the first opposable component 502 is not visible before migration of the dye has occurred from the dye area 540 to the dye viewing area 542. This gives a visual indication that flow through the chromatographic medium 506 has occurred and that the assay can be read and interpreted.

In an alternative, the dye area 540 contains a visible dye linked to a first member of an auxiliary specific binding pair that does not bind to any other specific binding partner in the device or to the analyte, and the dye viewing area 542 contains an immobilized second member of the auxiliary specific binding pair that binds only the first member of the auxiliary specific binding pair. This immobilizes the visible dye at the dye viewing area 542 when flow has occurred. Typically, the first member of the auxiliary specific binding pair is biotin and the second member of the auxiliary specific binding pair is avidin or streptavidin. Other first and second members of the auxiliary specific binding pair can be used. In this alternative, the dye area 540 and the dye viewing area 542 can be located as described above.

In another preferred alternative, the quantity of analyte or analyte analogue immobilized at the control zone 522 can be predetermined so that the quantity of labeled second specific binding partner that binds to the analyte or analyte analogue at the control zone 522 gives an intensity of label at the control zone 522 equivalent to that seen in the detection zone 520 when a predetermined concentration of analyte is present in the sample. Thus, the quantity of analyte or analyte analogue at the control zone 522 can be preselected so that the intensity of label at the control zone 522 and the detection zone 520 can be compared, thus giving an indication whether or not the concentration of the analyte to be tested is above or below a clinically important level.

An assay device according to FIG. 6 can be used to detect any analyte that can be detected by a sandwich immunoassay, as described above.

In one preferred alternative, the first and second specific binding partners are non-human monoclonal antibodies, most preferably murine monoclonal antibodies. In this alternative, the sample application zone 526 on the second opposable component 504 preferably contains a third specific binding partner as defined above. The third specific binding partner is an unlabeled, specific binding partner that is specific for human antibodies that bind to the non-human monoclonal antibody. The third specific binding partner can be immobilized or mobile. In this alternative, the chromatographic medium 506 further includes, in a validation zone 546, a fourth specific binding partner as defined above. The fourth specific binding partner is an immobilized specific binding partner that is specific for human antibodies that bind to the non-human monoclonal antibodies. In this alternative, the presence of detectable label at the validation zone 546 indicates interference in the assay caused by the presence of human-anti-mouse antibodies (HAMA). This detectable label is the second specific binding partner, which is a mobile labeled specific binding partner for the analyte. Typically, in this alternative, the third and fourth specific binding partners are mouse immunoglobulin G or a derivative or polymer of mouse immunoglobulin G, as described above.

The third specific binding partner serves to scavenge any human anti-mouse immunoglobulin G present in the sample. Only if the level of human anti-mouse immunoglobulin G antibodies is so high that the third specific binding partner in the sample application zone 526 cannot scavenge the antibodies would detectable label appear at the validation zone 546, thus indicating the presence of interference due to HAMA.

In one preferred alternative, the analyte is hCG. In this alternative, the first specific binding partner is preferably a monoclonal antibody specific for the a-subunit of hCG and the second specific binding partner is preferably a monoclonal antibody specific for the P subunit of hCG and not cross-reactive with luteinizing hormone (LH). Particularly preferred monoclonal antibodies for this analyte are described above.

As described above, an assay device according to FIG. 6 can be constructed to assay hormones such as TSH, FSH, or LH instead of hCG.

II. Analytes and Specific Binding Partners for Use with Assay Devices

The analytes suitable for detection with an assay device according to the present invention include antigens, haptens, and antibodies. Antigens detectable with the device include hemoglobin, Streptococcus A and B antigens, protein and glycoprotein hormones, antigens specific for the protozoan parasite Giardia, and viral antigens, including antigens specific for HIV and the Australia antigen specific for hepatitis.

One significant category of antigens detectable with the device is protein, polypeptide, and glycoprotein hormones. Such hormones include, but are not limited to, human chorionic gonadotropin (hCG), luteinizing hormone (LH), follicle stimulating hormone (FSH), and thyroid stimulating hormone (TSH), corticotropin-releasing hormone (CRH), growth hormone-releasing hormone (GHRH), prolactin, human growth hormone (hGH), β-lipotropin, corticotropin, β-endorphin, calcitonin, parathormone, human placental lactogen (hPL), insulin, glucagon, pancreatic polypeptide (PP), secretin, cholecystokinin-pancreozymin, motilin, vasoactive intestinal peptide, gastric inhibitory peptide, and erythropoietin. Antigens particularly suited to detection by assay devices according to the present invention include hCG, LH, FSH, and TSH.

Antibodies that can be assayed include antibodies to bacteria such as *Helicobacter pylori* and the viruses including HIV. Haptens detectable include haptens to which antibodies of sufficient specificity can be prepared.

One antigen for which devices according to the present invention are particularly suitable is hCG. The detection of hCG is used widely as a test for pregnancy. Clearly, high accuracy and high sensitivity are important in assay of hCG because the diagnosis of pregnancy or its absence has many social, psychological and medical consequences and it is crucial that such diagnoses be available as early as possible in a pregnancy and be highly accurate. Other antigens for which devices according to the present invention are particularly suitable are the closely related glycoprotein hormones TSH, FSH, and LH.

If the analyte is an antigen or a hapten and a sandwich procedure is used, the first and second specific binding partners are preferably antibodies. In many applications, it is preferable if the first and second specific binding partners are antibodies to different epitopes on the analyte but this is not necessarily required in the case of an antigen that has multiple copies of the same epitope, such as a viral capsid made up of repetitive protein subunits or a multi-subunit protein that contains multiple copies of the same polypeptide chain.

The antibodies can be polyclonal or monoclonal, and can be IgG, IgM, or IgA. In some applications, polyclonal antibodies are preferred, as their natural variability may allow more accurate detection in systems or antigenic polymorphisms exist or may exist. However, where extreme sensitivity and freedom from cross-reactivity is required, monoclonal antibodies are particularly suited for use with assay devices according to the present invention. Monoclonal antibodies are particularly suited for the detection of protein and glycoprotein hormones, such as hCG, FSH, LH, and TSH.

One particular analyte for which monoclonal antibodies are particularly suited is hCG. This is because of the need to avoid cross-reactivity between hCG and luteinizing hormone (LH). Therefore, a monoclonal antibody that is specific for the P subunit of hCG and lacks cross-reactivity with LH is preferably used as the labeled second specific binding partner for assay of hCG. In this assay, a monoclonal antibody that is specific for the (X subunit of hCG is preferably used as the first specific binding partner, the specific binding partner immobilized on the chromatographic medium at the detection zone. This is an example of a two-antibody sandwich immunoassay employing monoclonal antibodies, an assay format described in U.S. Pat. No. 4,376,110 to David et al. and in U.S. Pat. No. 4,486,530 to David et al, both incorporated herein by this reference.

Where the analyte is a hapten and a sandwich assay procedure is used, it is strongly preferred that the first and second specific binding partners be antibodies of different epitopes; otherwise, there may be an undesirable competition reaction set up that may interfere with binding of a complex of the labeled specific binding partner and the analyte to the immobilized second specific binding partner. It is recognized that not all haptens are large enough to accommodate more than one epitope; however, some haptens that are not large enough to induce antibody formation efficiently when injected by themselves are nevertheless large enough that they possess more than one epitope. In cases where antibodies to more than one epitope for a hapten cannot be obtained, competitive immunoassay procedures are generally preferred.

When the analyte is an antibody, and a sandwich assay procedure is used, the labeled specific binding partner is typically a labeled antibody that binds to the analyte on the basis of species, class, or subclass (isotype) specificity. It is highly preferred that the labeled specific binding partner to an antibody analyte binds to the constant region of the antibody analyte, in order to prevent interference. Where the analyte is an antibody, the unlabeled, immobilized specific binding partner is preferably an antigen, a hapten, or an antigen or hapten analogue for which the antibody analyte is specific.

In some applications, it is desirable to employ indirect labeling. For example, in testing for Giardia antigen, an IgM antibody can be used that may be difficult to label directly. In that case, a secondary specific binding partner specific for a mobile second specific binding partner can be labeled. Typically, the labeled secondary specific binding partner binds to the antibody that is mobile on the basis of species, class, or subclass specificity. As an alternative to the use of a secondary specific binding partner, the mobile specific binding partner can be conjugated to biotin and an avidin-conjugated or streptavidin-conjugated label can be used.

As indicated above, the chromatographic medium has a detection zone that contains an immobilized specific binding partner to the analyte. The immobilized specific binding partner can be bound to the chromatographic medium by either covalent or noncovalent means; covalent means are generally preferred. Methods for immobilizing specific binding partners, particularly antibodies, on a chromatographic medium such as nitrocellulose or other solid phases are well known in the art and need not be described further here. Such methods are described, for example, in P. Tijssen, "Practice and Theory of Enzyme Immunoassays" (Elsevier, Amsterdam, 1985), ch. 13, pp. 297–328.

In some embodiments, particularly those of FIGS. 5 and 6, the analyte or an analyte analogue is bound to the chromatographic medium. Analyte analogues include, but are not limited to, the analyte stably covalently or noncovalently attached to a protein or another molecule that is, in turn, attached to the chromatographic medium. The analyte analogue can include a spacer. Typically, if a spacer is used, it includes saturated hydrocarbon moieties, but oxygen and nitrogen atoms can also be included. Typically, the spacer is about 10 Å to about 30 Å in length, but other lengths can be used. Methods of immobilization of both macromolecules and small molecules to solid supports are well known in the art and are described, for example, in G. T. Hermanson et al., "Immobilized Affinity Ligand Techniques" (Academic Press, Inc., San Diego, 1992).

EXAMPLES

The invention is illustrated by the following Examples. These examples are for illustrative purposes only and are not to be construed as limiting the scope of the invention in any manner.

Example 1

Assay Device for hCG Employing One Chromatographic Medium with One Labeled Specific Binding Partner An assay device for detecting hCG employing one chromatographic medium with one labeled specific binding partner is constructed according to FIG. 4.

The first and second opposable components are solid bleached sulfite, lined with Lexan, and are joined by a hinge of solid bleached sulfite. On the first opposable component is located a chromatographic medium of 18 mm wide Millipore SPHF nitrocellulose (Millipore, Bedford, Mass.). At the first and second end of the chromatographic medium are located absorbers of Ahlstrom 939 cellulose (Ahlstrom Filtration, Holly Springs, Pa.). The chromatographic medium is laminated to a 16-inch-long split-flow subassembly using a 4-inch-wide Lexan strip and transfer adhesive (3M Grade 465 Transfer Adhesive, 3M, Minneapolis, Minn.). The chromatographic medium includes a detection zone that has murine monoclonal antibody against the a subunit of hCG at 4 mg/ml in striping buffer (5 mM potassium phosphate, pH 7.5) as the first specific binding partner. The chromatographic medium also includes a reference zone that has goat anti-mouse IgG antibody at 0.5 mg/ml in striping buffer as the third specific binding partner. The chromatographic medium also includes a validation zone that has murine monoclonal antibody against cc-fetoprotein (AFP) at 2.0 mg/ml in striping buffer as the fifth specific binding partner. This murine monoclonal antibody is used at the validation zone as immunologically indifferent mouse IgG; it is not being used as an antibody, and could be replaced by any other source of mouse IgG. Appropriate binding partners are striped: the first specific binding partner at the detection zone, the third specific binding partner at the reference zone, and the fifth specific binding partner at the validation zone. The chromatographic medium includes blue dye near the first end of the chromatographic medium to serve as the resolubilizable visible dye.

A conjugate of colloidal carbon-labeled monoclonal antibody to the β-subunit of hCG is prepared according to the methods of U.S. Pat. No. 5,529,901 to Van Doorn et al. and used for the labeled second specific binding partner. The conjugate stock solution is 5 mM potassium phosphate, pH 7.5. The conjugate stock solution is diluted 1:2 in conjugate diluent (2.5% casein, 5 mM potassium phosphate, pH 7.5, and 8% sucrose).

The conjugate pad is nonwoven polyester (Hollingsworth & Vose 7760). The first and third portions of the conjugate pad are impregnated with conjugate stock solution while the second portion of the conjugate pad is impregnated with conjugate diluent.

The sample application zone on the second opposable component is extruded cellulose acetate (American Filtrona R-19131). The sample application zone contains, in sample treatment buffer (phosphate buffered saline, pH 7.4, 2% bovine serum albumin, and 4% Triton X-100), 0.5 mg/ml of PolyMAK 33, a heterophilic scavenger antibody (Boehringer Mannheim), 12 μg/ml of monoclonal anti-LH antibody (Hybritech 120119, San Diego, Calif.), and 1 mg/ml of bovine IgG. The sample application zone is then laminated to the device.

The device as constructed detects hCG.

Figure 7:
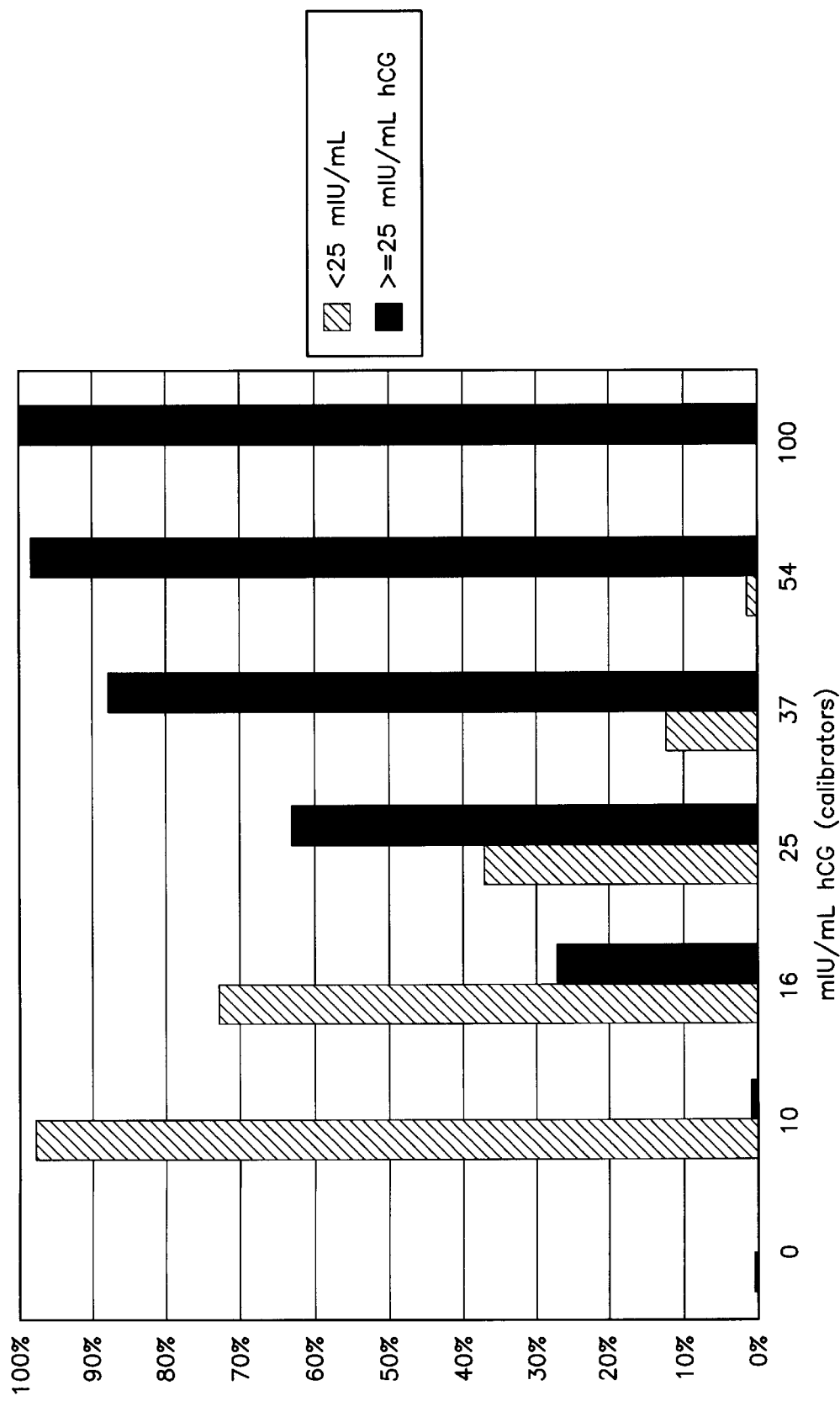
FIG. 7 is a histogram of results from Example 1, showing the semiquantitative determination of hCG concentration by the device of Example 1.

One set of test results for the device, using a wide range of hCG concentrations, is shown in Table 1. Another set of test results for the device, using a narrower range of hCG concentrations, is shown in Table 2. A histogram of the test results of Table 2 is shown in FIG. 7. The results of Table 2 and FIG. 7 clearly show that the device of Example 1 can distinguish a hCG level of less than 25 mIU/ml from a hCG level equal to or greater than 25 mIU/ml, and thus can perform a semiquantitative determination of the hCG level of a sample.

TABLE 1

RESULTS OF USING DEVICE OF EXAMPLE 1

Percent of Devices Yielding Results As:

| hCG, mIU/ml | − | +/− (<25 mIU/ml) | + (≧25 mIU/ml) |
|---|---|---|---|
| 0 | 100 | 0 | 0 |
| 10 | 0 | 100 | 0 |
| 25 | 0 | 20 | 80 |
| 50 | 0 | 0 | 100 |
| 400 | 0 | 0 | 100 |
| 10000 | 0 | 0 | 100 |
| 250000 | 0 | 0 | 100 |
| 500000 | 0 | 20 | 80 |
| 0 + HAMA | 100 | 0 | 0 |

TABLE 2

RESULTS OF USING DEVICE OF EXAMPLE 1
WITH NARROWER RANGE OF hCG CONCENTRATIONS

| hCG, mIU/ml | <25 mIU/ml | | >25 mIU/ml | | False Results | | Invalid | |
|---|---|---|---|---|---|---|---|---|
| | N | % | N | % | N | % | N | % |
| 0 | 1 | 0.4% | 0 | 0.0% | 1 | 0.4% | 0 | 0.0% |
| 10 | 243 | 93.5% | 2 | 0.8% | 3 | 1.2% | 12[b] | 4.6% |

TABLE 2-continued

RESULTS OF USING DEVICE OF EXAMPLE 1
WITH NARROWER RANGE OF hCG CONCENTRATIONS

| hCG, | <25 mIU/ml | | >25 mIU/ml | | False Results | | Invalid | |
|---|---|---|---|---|---|---|---|---|
| mIU/ml | N | % | N | % | N | % | N | % |
| 16.2[a] | 190 | 73.1% | 70 | 26.9% | 0 | 0.0% | 0 | 0.0% |
| 25 | 96 | 36.9% | 163 | 62.7% | 0 | 0.0% | 1 | 0.4% |
| 36.8[a] | 32 | 12.3% | 228 | 87.7% | 0 | 0.0% | 0 | 0.0% |
| 54.4[a] | 4 | 1.5% | 256 | 98.5% | 0 | 0.0% | 0 | 0.0% |
| 100 | 0 | 0.0% | 255 | 98.1% | 0 | 0.0% | 5 | 1.9% |

260 tests run each hCG concentration.
a determined by quantitative ELISA test of U.S. Pat. No. 4,376,110 to David et al.
[b]All on same test card

Example 2

Assay Device for hCG Employing One Chromatographic Medium with Two Labeled Specific Binding Partners An assay device employing one chromatographic medium with two labeled specific binding partners is constructed according to FIG. 2. This device is constructed substantially according to the device of Example 1 except that the third specific binding partner is rabbit anti-goat IgG and the conjugate pad contains, in the third portion, goat IgG labeled with colloidal carbon. Colloidal carbon labeling is performed as in Example 1.

This device detects hCG.

Example 3

Assay Device for hCG Employing One Chromatographic Medium with One Labeled Specific Binding Partner and On-Board Control An assay device employing one chromatographic medium with one labeled specific binding partner and an on-board control is constructed according to FIG. 6. This device is constructed substantially according to the device of Example 1 except that the reference zone is replaced with a control zone and the third specific binding partner at the reference zone is replaced with hCG immobilized at the control zone to provide an on-board control.

ADVANTAGES OF THE PRESENT INVENTION

Chromatographic assay devices according to the present invention provide an advantage in being constructed of opposable elements. This use of opposable elements provides great versatility, as it permits the performance of reactions in a number of different sequences. This is possible because the use of such opposable elements allows the delivery of reagents to precisely defined regions of a chromatographic medium or other reaction component.

The use of opposable elements also provides optimum performance with minimum consumption of reagents by ensuring that reagents are not wasted by being sequestered in dead volumes of apparatus. The use of opposable components also provides optimum containment of possibly contaminated blood samples, such as those containing HIV or hepatitis virus.

Another advantage of assay devices according to the present invention lies in the ability of the devices to use pressure to drive fluids from one opposable component to the other and through the chromatographic medium and the control of pressure applied so that the pressure is optimum for each assay to be carried out. This accelerates the assay process and allows the performance of operations such as extraction within the assay device. It also reduces the dead volume of reagents remaining in components, allowing the use of smaller samples and smaller quantities of expensive or hard-to-purify reagents such as labeled antibodies.

Additionally, chromatographic assay devices according to the present invention allow the rapid and accurate detection of clinically important analytes, particularly hCG, assayed as a pregnancy test, as well as other antigens, including protein and glycoprotein hormones.

Assay devices according to the present invention also provide a semi-quantitative indication of the concentration of the analyte being assayed by a direct visual comparison of the intensities of label at the detection zone and the reference zone. This allows such a semi-quantitative determination to be carried out in a single assay device, thereby avoiding the need for multiple assays employing multiple samples. Assay devices according to the present invention also provide a timing control to give a direct visual indication that flow through the chromatographic medium has occurred and the assay can be read and interpreted.

Another advantage of assay devices according to the present invention is the use of a validation zone to indicate freedom from anti-murine antibodies present in the sample when murine monoclonal antibodies are used in the assay device. This gives a direct visual control for another source of interference.

The use of colloidal carbon labels in a resolubilizable form provides extremely rapid kinetics of labeling. This aids in the separation of contaminants and improves the performance of the assay.

Extraction of biological samples such as blood, sputum, or feces can be performed directly in the device, reducing the quantity of contaminated material that must be disposed and reducing the likelihood of accidental infection of physicians, technicians, or the public by such contaminated material.

Test methods using the devices according to the present invention have a wide dynamic range particularly suitable for the assay of analytes in whole blood samples, increasing the quantity of sample reaching the detection zone by the use of a unidirectional assay and therefore increasing the sensitivity of the assay. Additionally, the present invention allows for any desired length of preincubation of the reactants, and provides more homogeneous mixing of the analyte and labeled specific binding partner.

Although the present invention has been described in considerable detail, with reference to certain preferred versions thereof, other versions and embodiments are possible. These versions include other arrangements of two-assay devices that operate by the basic principles described herein and utilize the principles of: (i) direct visual timing control; or (ii) use of a validation zone to indicate the absence of interference caused by HAMA In particular, devices according to the present invention can be adapted to make use of radial or circumferential flow through a chromatographic medium instead of linear flow. The present invention further encompasses variations in which the two components of the device are not held in a permanently fixed arrangement, but can be separated and brought together to perform the assay, such as by electrical or magnetic forces or by using a separable fastener such as a hook-and-eye fabric, for example, Velcro™. Therefore, the scope of the invention is determined by the following claims.

We claim:

1. A chromatographic assay device for detection or determination of an analyte in a test sample comprising:
   (a) a first opposable opponent including:
      (i) a first chromatographic medium having first and second ends and an immobilized first specific binding partner for the analyte in a detection zone;
      (ii) a conjugate pad in operable contact with the first end of the first chromatographic medium so that fluid applied to the conjugate pad flows from the conjugate pad to the first end of the first chromatographic medium, the conjugate pad including:
         (A) a first portion containing a labeled second specific binding partner for the analyte in resolubilizable form;
         (B) a second portion; and
         (C) a third portion containing a labeled second specific binding partner for the analyte in resolubilizable form, the second portion separating the first portion and the third portion; and
      (iii) a second chromatographic medium having first and second ends and having immobilized thereon in a reference zone a third specific binding partner, other than the analyte or an analyte analogue, that specifically binds the labeled second specific binding partner for the analyte and does not bind the analyte, the first end of the second chromatographic medium being in operable contact with the conjugate pad so that fluid applied to the conjugate pad flows from the conjugate pad to the first end of the second chromatographic medium; and
   (b) a second opposable component including a sample application zone; wherein the first and second opposable components are brought into opposition to apply a sample applied to the sample application zone to the conjugate pad to resolubilize the labeled second specific binding partner so that the sample and the resolubilized labeled second specific binding partner in the first portion of the conjugate pad are applied to the first chromatographic medium and the sample and the resolubilized labeled second specific binding partner in the third portion of the conjugate pad are applied to the second chromatographic medium for detection of the analyte.

2. The chromatographic assay device of claim 1 wherein the label is a colloidal particle label.

3. The chromatographic assay device of claim 2 wherein the colloidal particle label is a colloidal carbon label.

4. The chromatographic assay device of claim 1 wherein the label is a visually detectable label.

5. The chromatographic assay device of claim 1 wherein the sample application zone contains at least one reagent for treatment of the sample.

6. The chromatographic assay device of claim 1 wherein the analyte is selected from the group consisting of chorionic gonadotropin (hCG), luteinizing hormone (LH), follicle stimulating hormone (FSH), thyroid stimulating hormone (TSH), corticotropin-releasing hormone (CRH), growth hormone-releasing hormone (GHRH), prolactin, human growth hormone (hGH), β-lipotropin, corticotropin, β-endorphin, calcitonin, parathormone, human placental lactogen (hPL), insulin, glucagon, pancreatic polypeptide (PP), secretin, cholecystokinin-pancreozymin, motilin, vasoactive intestinal peptide, gastric inhibitory peptide, and erythropoietin.

7. The chromatographic assay device of claim 6 wherein the analyte is selected from the group consisting of hCG, TSH, LH, and FSH.

8. The chromatographic assay device of claim 7 wherein the analyte is hCG.

9. The chromatographic assay device of claim 8 wherein the first specific binding partner is a monoclonal antibody specific for the a subunit of hCG and the second specific binding partner is a monoclonal antibody specific for the β subunit of hCG and not cross-reactive with luteinizing hormone.

10. The chromatographic assay device of claim 1 where the first opposable component further includes a resolubilizable visible dye, the resolubilizable visible dye being located either in an area between the detection zone and the second end of the first chromatographic medium or in an absorber that is optionally present and, if present, is in operable contact with the second end of the first chromatographic medium to absorb fluid from the first chromatographic medium, and the second opposable component has an aperture for viewing of the visible dye when flow has occurred through the first chromatographic medium and the assay can be read and interpreted.

11. The chromatographic assay device of claim 1 wherein the first opposable component further includes: (i) a resolubilizable visible dye linked to a first member of an auxiliary specific binding pair that does not bind to any other specific binding partner in the device or to the analyte, the resolubilizable visible dye being located either in an area between the detection zone and the second end of the first chromatographic medium or in an absorber that is optionally present, the absorber, if present, being in operable contact with the second end of the first chromatographic medium to absorb fluid from the second end of the first chromatographic medium and (ii) an immobilized second member of the auxiliary specific binding pair that binds only the first member of the auxiliary specific binding pair in a dye viewing area, and the second opposable component has an aperture for viewing of the visible dye when flow has occurred through the first chromatographic medium and the assay can be read and interpreted.

12. The chromatographic assay device of claim 11 wherein the first member of the auxiliary specific binding pair is biotin and the second member of the auxiliary specific binding pair is avidin or streptavidin.

13. The device of claim 1 wherein the sample application zone contains a fourth specific binding partner that is specific for human antibodies that bind the second specific binding partner and wherein the first chromatographic medium contains, in a validation zone, a fifth immobilized specific binding partner that is specific for human antibodies that bind the second specific binding partner such that the presence of detectable label at the validation zone indicates interference, the validation zone being located closer to the first end of the first chromatographic medium than is the detection zone.

14. The chromatographic assay device of claim 13 wherein the second specific binding partner is a non-human monoclonal antibody, the fourth specific binding partner is specific for human IgG antibodies that bind to the non-human monoclonal antibody, and the fifth immobilized specific binding partner is specific for human IgG antibodies that bind to the non-human monoclonal antibody.

15. The chromatographic assay device of claim 14 wherein the first and second specific binding partners are murine monoclonal antibodies, and wherein the fourth and fifth specific binding partners are each murine IgG or a polymer of murine IgG.

16. The chromatographic assay device of claim 13 wherein the fourth specific binding partner is immobilized in the sample application zone.

17. The chromatographic assay device of claim 13 wherein the fourth specific binding partner is mobile and located at the sample application zone.

18. A method for detecting or determining an analyte in a test sample comprising the steps of:
(a) applying the sample to the sample application zone on the second opposable component of the chromatographic assay device of claim 1;
(b) bringing the first and second opposable components of the chromatographic assay device into operable contact so that the second labeled specific binding partner in the first and third portions of the conjugate pad is resolubilized;
(c) allowing the sample and the resolubilized labeled second specific binding partner in the first portion of the conjugate pad to migrate through the first chromatographic medium and allowing the sample and the resolubilized labeled second specific binding partner in the third portion of the conjugate pad to migrate through the second chromatographic medium; and
(d) observing or measuring the labeled second specific binding partner bound to the first specific binding partner at the detection zone in order to detect or determine the analyte.

19. A chromatographic assay device for detection of an analyte in a sample comprising:
(a) a first opposable component having:
(i) a first chromatographic medium having a first functional zone containing an immobilized first reagent;
(ii) a first conjugate zone in operable contact with the first chromatographic medium so that fluid applied to the first conjugate zone flows to the first chromatographic medium, the first conjugate zone containing a second reagent in resolubilizable form;
(iii) a second chromatographic medium having a second functional zone containing an immobilized third reagent;
(iv) a second conjugate zone in operable contact with the second chromatographic medium so that fluid applied to the second conjugate zone flows to the second chromatographic medium, the second conjugate zone containing a fourth reagent in resolubilizable form; and
(v) an isolation zone that functionally isolates the first conjugate zone and the first chromatographic medium from the second conjugate zone and the second chromatographic medium; and
(b) a second opposable component having a sample application zone for applying the sample,
wherein when the first and second opposable components are brought into opposition, the sample applied to the sample application zone is applied to the first and second conjugate zones and resolubilizes the second and fourth resolubilizable reagents.

20. The chromatographic assay device of claim 19, wherein the first and second chromatographic media are formed of physically separate pieces of nitrocellulose material, and
wherein the first opposable component comprises a conjugate pad having a first portion constituting the first conjugate zone, a second portion constituting the second conjugate zone, and a third portion between the first and second portion and constituting the isolation zone.

21. The chromatographic assay device of claim 19, wherein the first and second chromatographic media are formed of a contiguous piece of nitrocellulose material with a separation area between the first and second functional zones, and
wherein the first opposable component comprises a conjugate pad over the separation area, the conjugate pad having a first portion constituting the first conjugate zone, a second portion constituting the second conjugate zone, and a third portion between the first and second portion and constituting the isolation zone.

22. The chromatographic assay device of claim 19, wherein the first and third reagents are unlabeled and the second and fourth reagents are labeled.

23. The chromatographic assay device of claim 22 wherein the label for the second and/or fourth reagent is a colloidal particle label.

24. The chromatographic assay of claim 23 wherein the colloidal particle label is a colloidal carbon label.

25. The chromatographic assay device of claim 22 wherein the label for the second and/or fourth reagent is a visually detectable label.

26. The chromatographic assay device of claim 19, wherein when the sample with the resolubilized second and fourth reagents are applied to the respective first and second chromatographic media, the second and fourth reagents are immobilized by the first and third reagents in the first and second functional zones, respectively.

27. The chromatography assay device of claim 19, wherein the first reagent is an unlabeled first specific binding partner for the analyte, the second reagent is a labeled second specific binding partner for the analyte, the third reagent is a third specific binding partner, other than the analyte or an analyte analogue, that specifically binds the labeled second specific binding partner for the analyte and does not specifically bind the analyte, and the fourth reagent is the labeled second specific binding partner for the analyte.

28. The chromatographic assay device of claim 19, wherein the first reagent is an unlabeled first specific binding partner for the analyte, the second reagent is a labeled second specific binding partner for the analyte, the third reagent is a third specific binding partner, other than the analyte or an analyte analogue, that does not specifically bind the analyte or a specific binding partner that specifically binds the analyte, and the fourth reagent is a labeled fourth specific binding partner that does not specifically bind the analyte or a specific binding partner that specifically binds the analyte, the third and fourth specific binding partners specifically binding each other.

29. The chromatographic assay device of claim 19, wherein the first reagent is an unlabeled first specific binding partner for the analyte, the second reagent is a labeled second specific binding partner for the analyte, the third reagent is the analyte or an analyte analogue, and the fourth reagents is the labeled second specific binding partner for the analyte.

30. The chromatographic assay device of claim 19, wherein the second functional zone contains a predetermined quantity of the third reagent so that a label generated by the fourth reagent in the second functional zone has an intensity equivalent to that of a label generated by the second reagent in the first functional zone when a predetermined concentration of analyte is present in the sample.

31. A method for detecting or determining an analyte in a sample using the chromatographic assay device of claim 30, comprising:
(a) applying the sample to the sample application zone on the second opposable component of the assay device;
(b) bringing the first and second opposable components of the chromatographic assay device into operable contact whereby the second and fourth reagents in the first and second conjugate zones are resolubilized;

(c) allowing the sample and the resolubilized second reagent to migrate through the first chromatographic medium and allowing the sample and the resolubilized fourth reagent to migrate through the second chromatographic medium;

(d) observing or measuring any label in the first functional zone to detect or determine the analyte; and (e) comparing intensities of labels in the first and second functional zones to determine a relative amount of the analyte present in the sample.

32. The chromatographic assay device of claim 19, wherein the first chromatographic medium further has a dye zone containing a resolubilizable visible dye and a dye viewing area, wherein the first functional zone is located between the dye zone and the first conjugate zone, and the dye zone is located between the dye viewing area and the first functional zone.

33. The chromatographic assay device of claim 32, wherein the first opposable component further has an absorber in operable contact with the first chromatographic medium and located farther away from the first conjugate zone than is the first functional zone so that fluid flown to the first functional zone from the first conjugate zone flows to the absorber, and wherein the dye zone and the dye viewing area are located in the absorber.

34. The chromatographic assay device of claim 32, wherein the resolubilizable visible dye is linked to a first member of an auxiliary specific binding pair that does not specifically bind to any other specific binding partner in the device or to the analyte, and wherein the dye viewing area contains an immobilized second member of the auxiliary specific binding pair that specifically binds only the first member of the auxiliary specific binding pair.

35. The chromatographic assay device of claim 34 wherein the first member of the auxiliary specific binding pair is biotin and the second member of the auxiliary specific binding pair is avidin or streptavidin.

36. A method for detecting or determining an analyte in a sample using the chromatographic assay device of claim 32, comprising:

(a) applying the sample to the sample application zone on the second opposable component of the assay device;

(b) bringing the first and second opposable components of the chromatographic assay device into operable contact whereby the second reagent in the first conjugate zone is resolubilized;

(c) allowing the sample and the resolubilized second reagent to migrate through the first chromatographic medium;

(d) observing any dye in the dye viewing area to determine whether the migration has occurred through the first chromatographic medium; and (e) observing or measuring any label in the first functional zone to detect or determine the analyte.

37. The chromatographic assay device of claim 19, wherein the second opposable component comprises a backing having first and second designated areas corresponding in position to the first and second functional zones, respectively, so that when the first and second opposable components are brought into opposition, the first and second functional zones are visible through the first and second designated areas, respectively.

38. The chromatographic assay device of claim 19, further comprising an attachment mechanism that attaches the first and second opposable components to each other and allows them to be brought into opposition.

39. The chromatographic assay device of claim 19 wherein the sample application zone contains at least one reagent for treatment of the sample.

40. The chromatographic assay device of claim 19 wherein the analyte is selected from the group consisting of chorionic gonadotropin (hCG), luteinizing hormone (LH), follicle stimulating hormone (FSH), thyroid stimulating hormone (TSH), cotricotropin-releasing hormone (CRH), growth hormone-releasing hormone (GHRH), prolactin, human growth hormone (hGH), β-lipotropin, corticotropin, β-endorphin, calcitonin, parathormone, human placental lactogen (hPL), insulin, glucagon, pancreatic polypeptide (PP), secretin, cholecystokinin-pancreozymin, motilin, vasoactive intestinal peptide, gastric inhibitory paptide, and erythropoietin.

41. The chromatographic assay device of claim 40 wherein the analyte is selected from the group consisting of hCG, TSH, LH, and FSH.

42. The chromatographic assay device of claim 41 wherein the analyte is hCG.

43. The chromatographic assay device of claim 19 wherein the first specific binding partner is a monoclonal antibody specific for the a subunit of hCG and the second specific binding partner is a monoclonal antibody specific for the β subunit of hCG and not cross-reactive with luteinizing hormone.

44. The chromatographic assay device of claim 19 wherein the sample application zone contains a fifth specific binding partner that is specific for human antibodies that bind the second specific binding partner, and wherein the first chromatographic medium further has a validation zone containing a sixth immobilized specific binding partner that is specific for human antibodies that bind the second specific binding partner such that the presence of detectable label at the validation zone indicates interference, the validation zone being located between the first conjugate zone and the first functional zone.

45. The chromatographic assay device of claim 44 wherein the second specific binding partner is a non-human monoclonal antibody, the fifth specific binding partner is specific for human IgG antibodies that bind to the non-human monoclonal antibody, and the sixth specific binding partner is specific for human IgG antibodies that bond to the non-human monoclonal antibody.

46. The chromatographic assay device of claim 44 wherein the fifth specific binding partner is immobilized in the sample application zone.

47. The chromatographic assay device of claim 44 wherein the fifth specific binding partner is mobile and located at the sample application zone.

48. The chromatographic assay device of claim 45 wherein the first and second specific binding partners are murine monoclonal antibodies, and wherein the fifth and sixth specific binding partners are each murine IgG or a derivative or polymer of murine IgG.

49. A method for detecting or determining an analyte in a sample using the chromatographic assay device of claim 44, comprising:

(a) applying the sample to the sample application zone on the second opposable component of the assay device;

(b) bringing the first and second opposable components of the chromatographic assay device into operable contact whereby the second reagent in the first conjugate zone is resolubilized;

(c) allowing the sample and the resolubilized second reagent to migrate through the first chromatographic medium;

(d) observing or measuring any label in the first functional zone to detect or determine the analyte; and (e) observing any label in the validation zone to determine whether any interference is present.

50. A method for detecting or determining an analyte in a sample using the chromatographic assay device of claim 19, comprising:

(a) applying the sample to the sample application zone on the second opposable component of the assay device;

(b) bringing the first and second opposable components of the chromatographic assay device into operable contact whereby the second and fourth reagents in the first and second conjugate zones are resolubilized;

(c) allowing the sample and the resolubilized second reagent to migrate through the first chromatographic medium and allowing the sample and the resolubilized fourth reagent to migrate through the second chromatographic medium;

(d) observing or measuring any label in the first functional zone to detect or determine the analyte; and (e) observing or measuring any label in the second functional zone to determine whether the assay has run properly.

* * * * *